(12) United States Patent
Pop et al.

(10) Patent No.: US 7,879,871 B2
(45) Date of Patent: *Feb. 1, 2011

(54) CRYSTALLINE FORMS OF TIOTROPIUM BROMIDE

(75) Inventors: Mihaela Maria Pop, Amsterdam (NL); Stéphanie Houdayer Mulder, Maarssen (NL); Mimoun Lamkadmi, Rotterdam (NL)

(73) Assignee: Boehringer Ingelheim International GmbH, Ingelheim (DE)

( * ) Notice: Subject to any disclaimer, the term of this patent is extended or adjusted under 35 U.S.C. 154(b) by 1192 days.

This patent is subject to a terminal disclaimer.

(21) Appl. No.: 11/381,076

(22) Filed: May 1, 2006

(65) Prior Publication Data

US 2007/0092453 A1   Apr. 26, 2007

Related U.S. Application Data

(60) Provisional application No. 60/676,807, filed on May 2, 2005.

(51) Int. Cl.
*A61K 31/46* (2006.01)
*C07D 451/10* (2006.01)

(52) U.S. Cl. .................................... 514/291; 546/89
(58) Field of Classification Search .............. 546/89; 514/291

See application file for complete search history.

(56) References Cited

U.S. PATENT DOCUMENTS

| | | | |
|---|---|---|---|
| 3,673,195 A | 6/1972 | Yoneda et al. | |
| 3,808,263 A | 4/1974 | Yoneda et al. | |
| 4,353,922 A | 10/1982 | Pfister | |
| 4,855,422 A | 8/1989 | Grimminger et al. | |
| 5,610,163 A | 3/1997 | Banholzer et al. | |
| 5,770,738 A | 6/1998 | Banholzer et al. | |
| 6,433,027 B1 | 8/2002 | Bozung et al. | |
| 6,486,321 B2 | 11/2002 | Banholzer et al. | |
| 6,506,900 B1 | 1/2003 | Banholzer et al. | |
| 6,608,055 B2 | 8/2003 | Sieger et al. | |
| 6,747,154 B2 | 6/2004 | Brandenburg et al. | |
| 6,777,423 B2 | 8/2004 | Banholzer et al. | |
| 6,908,928 B2 | 6/2005 | Banholzer et al. | |
| 2002/0110529 A1 | 8/2002 | Bechtold-Peters et al. | |
| 2002/0111363 A1 | 8/2002 | Drechsel et al. | |
| 2002/0133010 A1 | 9/2002 | Banholzer et al. | |
| 2002/0193392 A1 | 12/2002 | Schmelzer et al. | |
| 2002/0193394 A1 | 12/2002 | Disse | |
| 2003/0171586 A1 | 9/2003 | Banholzer et al. | |
| 2004/0002510 A1 | 1/2004 | Bender et al. | |
| 2004/0018153 A1 | 1/2004 | Schmelzer | |
| 2004/0039011 A1 | 2/2004 | Disse | |
| 2004/0087793 A1 | 5/2004 | Banholzer et al. | |
| 2005/0038252 A1 | 2/2005 | Morschhaeuser et al. | |
| 2005/0143410 A1 | 6/2005 | Pfrengle et al. | |

2006/0047120 A1   3/2006   Lock et al.

FOREIGN PATENT DOCUMENTS

| | | |
|---|---|---|
| DE | 1 166 787 | 4/1964 |
| DE | 101 11 843 A1 | 9/2002 |
| EP | 0 418 716 A1 | 3/1991 |
| GB | 845056 | 8/1960 |
| GB | 955535 | 4/1964 |
| GB | 1350928 | 4/1974 |
| SI | 9011744 B | 12/1999 |
| SI | 9011744 B | 12/1999 |
| WO | WO 94/13262 A1 | 6/1994 |
| WO | WO 00/07567 A1 | 2/2000 |
| WO | WO 02/30928 * | 4/2002 |
| WO | WO 02/30928 A1 | 4/2002 |
| WO | WO 02/36104 A2 | 5/2002 |
| WO | WO 02/38154 A1 | 5/2002 |
| WO | WO 02/051840 A1 | 7/2002 |
| WO | WO03/000265 | 1/2003 |

OTHER PUBLICATIONS

U.S. Appl. No. 11/381,079, commonly assigned to Boehringer Ingelheim Corporation.*
Atkinson, E.R. et al: "Parasympatholytic (Anticholinergic) Esters of the Isomeric 2-tropanols. 1. Glycolates"; J Med Chem; 1977, vol. 20, No. 12, pp. 1612-1617.
Disse, B. et al; "Tiotropium (Spiriva™): Mechanistical Considerations and Clinical Profile in Obstructive Lung Disease"; Life Sciences, vol. 64, Nos. 6/7, pp. 457-464, 1999, XP-002268933.
Foster, R. et al; "Further New Tropine Derivative"; Journal of the Chemical Society, (1957) pp. 3575-3578.
Petrovic, G. et al; "Synthesis of Acetyl Scopine. Intramolecular Reactions of N-Carbethoxy Nortropine-3alpha-benzenesulfenate"; Synlett, 1999, No. 5, pp. 635-637.
Stahl, P. H. et al, "Handbook of Pharmaceutical Salts Properties, Selection and use", Wiley-VCH, Weinheim-New York (2002), p. 98 XP 002268934.
N-Butylscopolammonium Bromide Buscopan), Merck Index, 10th ed, pp. 219-220 (1983).
Ipratropium Bromide (Atrovent), Merck Index, 10th Ed., (1983), p. 733.
The Merck Index, 11th ed (1989), Merck and Co., Inc., pp. 242 and 802-803.
Accession Number (AN) : 1998:8089, USAN, Generic Name (CN) : Tiotropium Bromide, CAS Registry No. (RN) ; 139404-48-1, printout ("the USAN reference") (1998).
Nyberg, Klas, et al; Preparation of Methyl Dithienylglycolates, Magnetically Nonequivalen Protons in Dithienylglycolates; Acta Chamica Scandinavica 24 (1970) No. 5 1590-1596.

(Continued)

*Primary Examiner*—Susannah Chung
*Assistant Examiner*—Alicia L Otton
(74) *Attorney, Agent, or Firm*—Michael P. Morris; Wendy A. Petka

(57) ABSTRACT

The invention relates to a new crystalline forms of tiotropium bromide, processes for preparing them and their use for preparing a pharmaceutical composition for the treatment of respiratory complaints, particularly for the treatment of COPD (chronic obstructive pulmonary disease) and asthma.

58 Claims, 15 Drawing Sheets

OTHER PUBLICATIONS

Weiner, Norman, Goodman & Gilman, The Pharmacological Basis of Therapeutics, 6th Ed. p. 130, Valpin; (MacMillan 1980).

2010 USPC Official, Dec. 1, 2009-Sep. 30, 2010 General Chapters: <941> X-Ray Diffraction.

* cited by examiner

CRYSTALLINE FORMS OF TIOTROPIUM BROMIDE

RELATED APPLICATIONS

This application claims benefit and priority to U.S. provisional application No. 60/676,807, filed May 2, 2005, the content of which is hereby incorporated by reference in its entirety.

FIELD OF THE INVENTION

The invention relates to a new crystalline forms of tiotropium bromide, processes for preparing them and their use for preparing a pharmaceutical composition for the treatment of respiratory complaints, particularly for the treatment of COPD (chronic obstructive pulmonary disease) and asthma.

BACKGROUND TO THE INVENTION

Tiotropium bromide is known from European Patent Application EP 418 716 A1 and has the following chemical structure:

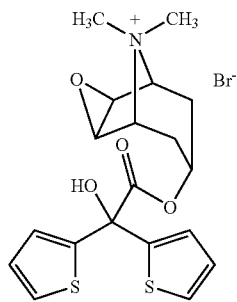

Tiotropium bromide is a highly effective anticholinergic with a long-lasting effect, which may be used to treat respiratory complaints, particularly COPD (chronic obstructive pulmonary disease) and asthma. By tiotropium is meant the free ammonium cation.

Tiotropium bromide is preferably administered by inhalation. Suitable inhalable powders packed into appropriate capsules (inhalettes) may be used. Alternatively, it may be administered by the use of suitable inhalable aerosols. These also include powdered inhalable aerosols which contain, for example, HFA134a, HFA227 or mixtures thereof as propellent gas.

The correct manufacture of the abovementioned compositions which are suitable for use for the administration of a pharmaceutically active substance by inhalation is based on various parameters which are connected with the nature of the active substance itself. In pharmaceutical compositions which are used like tiotropium bromide in the form of inhalable powders or inhalable aerosols, the crystalline active substance is used in ground (micronised) form for preparing the formulation. Since the pharmaceutical quality of a pharmaceutical formulation requires that the active substance should always have the same crystalline modification, the stability and properties of the crystalline active substance are subject to stringent requirements from this point of view as well.

The aim of the invention is therefore to provide a new crystal forms of the compound tiotropium bromide which meet the high demands mentioned above that are made of any pharmaceutically active substance.

DETAILED DESCRIPTION OF THE INVENTION

Figure 1:
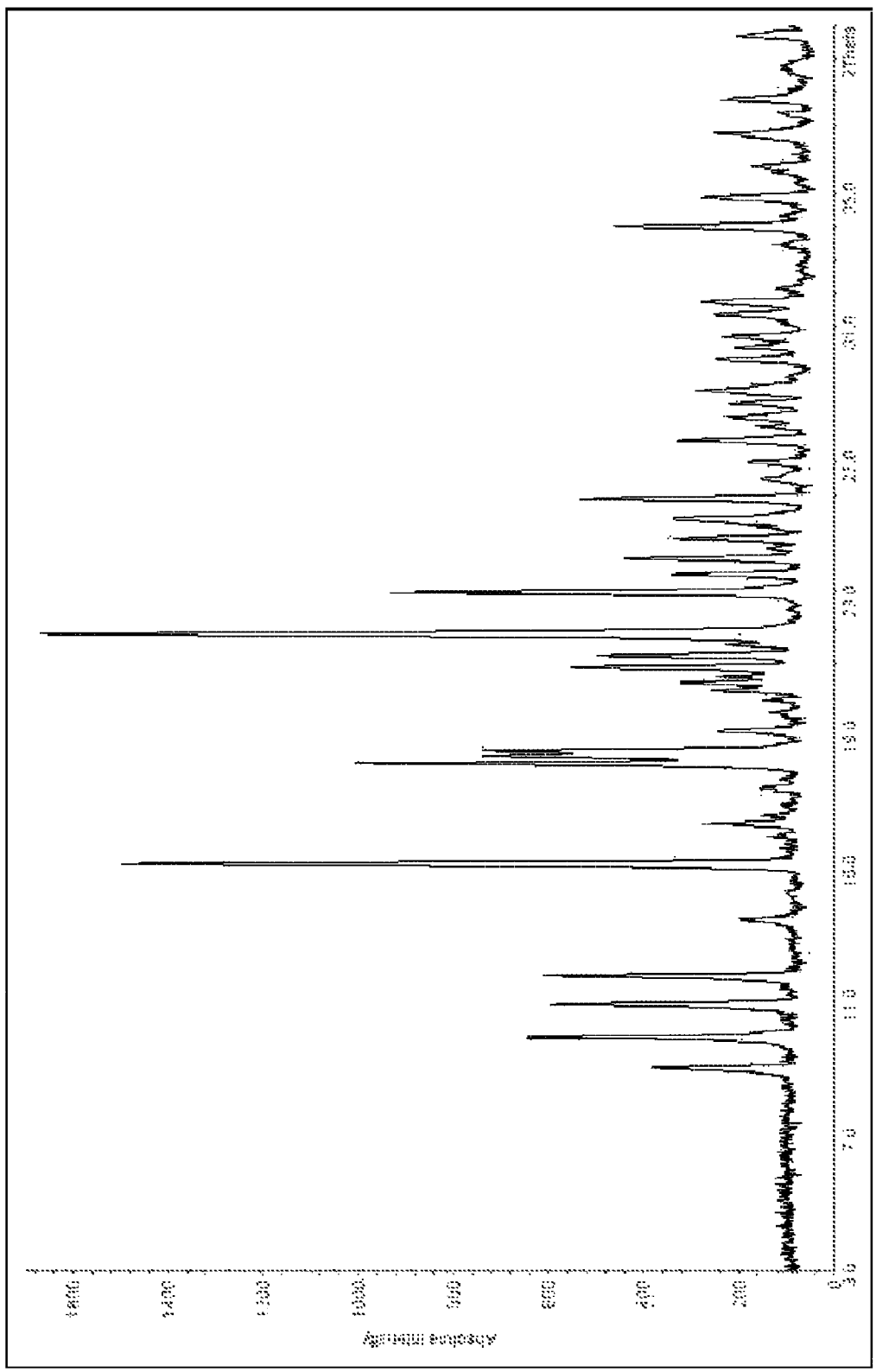
FIG. 1: X-ray powder diffraction of anhydrous crystalline tiotropium bromide

It has been found that, depending on the choice of the conditions which may be used during the purification of the crude product obtained after industrial production, tiotropium bromide may be obtained in different crystalline modifications.

It has been found that these different modifications can be decisively obtained by the choice of solvents used for the crystallisation and by the choice of the operating conditions selected during the crystallisation process.

It has surprisingly been found that, starting from the monohydrate of tiotropium bromide, which can be obtained in crystalline form by choosing specific reaction conditions and which was described in the prior art for the first time in WO 02/30928, an anhydrous crystal modification of tiotropium bromide may be obtained which meets the high requirements set out above and thereby solves the problem underlying the present invention.

Accordingly, in one embodiment the present invention relates to this crystalline anhydrous tiotropium bromide. Any reference made within the scope of the present invention to the term tiotropium bromide anhydrate is to be regarded as a reference to the crystalline anhydrous tiotropium bromide according to the invention.

The invention relates to this crystalline tiotropium bromide anhydrate which is characterized by an orthorhombic elementary cell with the parameters a=11.7420(4) Å, b=17.7960(7) Å, c=19.6280(11) Å, and cell volume=4101.5(3) Å$^3$ determined by X-ray structural analysis.

In another embodiment, the present invention relates to a novel crystalline solvates of tiotropium bromide. One aspect of the invention is directed to a crystalline 1,4-dioxane solvate of tiotropium bromide. In another aspect the present invention relates to a method of preparing the new crystalline 1,4-dioxane solvate of tiotropium bromide which is explained by way of example in the experimental section that follows.

The invention relates to this crystalline 1,4-dioxane solvate of tiotropium bromide which is characterized by a monoclinic elementary cell with the parameters a=13.6650(3) Å, b=12.0420(3) Å, c=13.7090(3) Å, β=103.8150(13)°, and cell volume=2190.61(9) Å$^3$ determined by X-ray structural analysis.

In another embodiment, the present invention relates to a crystalline ethanol solvate of tiotropium bromide. In another aspect the present invention relates to a method of preparing the new crystalline ethanol solvate of tiotropium bromide which is explained by way of example in the experimental section that follows.

The invention relates to this crystalline ethanol solvate of tiotropium bromide which is characterized by a monoclinic elementary cell with the parameters a=13.5380(2) Å, b=11.9830(2) Å, c=26.9410(5) Å, β=105.1990(6)°, and cell volume=4217.65(12) Å$^3$ determined by X-ray structural analysis.

In another embodiment, the present invention relates to a crystalline methanol solvate of tiotropium bromide. In another aspect the present invention relates to a method of preparing the new crystalline methanol solvate of tiotropium bromide which is explained by way of example in the experimental section that follows.

The invention relates to this crystalline methanol solvate of tiotropium bromide which is characterized by a monoclinic elementary cell with the parameters a=13.4420(2) Å, b=37.0890(5) Å, c=13.6290(2) Å, β=104.7050(10)°, and cell volume=6572.18(16) Å$^3$ determined by X-ray structural analysis.

In another embodiment, the present invention relates to a crystalline anisol solvate of tiotropium bromide. In another aspect the present invention relates to a method of preparing the new crystalline anisol solvate of tiotropium bromide which is explained by way of example in the experimental section that follows.

The invention relates to this crystalline anisol solvate of tiotropium bromide which is characterized by a X-ray powder diagram with the characteristic values d=12.99 Å; 8.84 Å; 7.96 Å; 6.84 Å; 6.55 Å; 5.76 Å; 5.40 Å; 4.88 Å; 4.43 Å; 4.21 Å; 4.14 Å; 3.73 Å; 3.58 Å; 3.41 Å; 3.27 Å; 3.18 Å; 3.00 Å; and 2.95 Å; inter alia.

In another embodiment, the present invention relates to a crystalline n-butanol solvate of tiotropium bromide. In another aspect the present invention relates to a method of preparing the new crystalline n-butanol solvate of tiotropium bromide which is explained by way of example in the experimental section that follows.

The invention relates to this crystalline n-butanol solvate of tiotropium bromide which is characterized by a X-ray powder diagram with the characteristic values d=9.83 Å; 10.93 Å; 13.38 Å; 13.54 Å; 15.34 Å; 17.95 Å; 19.77 Å; 20.83 Å; 21.41 Å; 24.15 Å; 24.56 Å; 25.03 Å; 25.66 Å; 26.03 Å; 26.95 Å; and 29.87 Å; inter alia.

In another embodiment, the present invention relates to a crystalline N,N-dimethylacetamide (=DMA) solvate of tiotropium bromide. In another aspect the present invention relates to a method of preparing the new crystalline DMA solvate of tiotropium bromide which is explained by way of example in the experimental section that follows.

The invention relates to this crystalline DMA solvate of tiotropium bromide which is characterized by a X-ray powder diagram with the characteristic values d=8.86 Å; 7.89 Å; 6.50 Å; 5.73 Å; 5.37 Å; 4.89 Å; 4.42 Å; 4.18 Å; 4.10 Å; 3.83 Å; 3.72 Å; 3.55 Å; 3.39 Å; 3.25 Å; 3.16 Å; and 2.95 Å; inter alia.

In another embodiment, the present invention relates to a crystalline N,N-dimethylformamide (=DMF) solvate of tiotropium bromide. In another aspect the present invention relates to a method of preparing the new crystalline DMF solvate of tiotropium bromide which is explained by way of example in the experimental section that follows.

The invention relates to this crystalline DMF solvate of tiotropium bromide which is characterized by a X-ray powder diagram with the characteristic values d=8.86 Å; 7.95 Å; 6.51 Å; 5.73 Å; 5.36 Å; 4.89 Å; 4.43 Å; 4.19 Å; 4.12 Å; 3.82 Å; 3.68 Å; 3.57 Å; 3.40 Å; 3.25 Å; 3.16 Å; and 2.96 Å; inter alia.

In another embodiment, the present invention relates to a isopropanol solvate of tiotropium bromide. In another aspect the present invention relates to a method of preparing the new crystalline isopropanol solvate of tiotropium bromide which is explained by way of example in the experimental section that follows.

The invention relates to this crystalline isopropanol solvate of tiotropium bromide which is characterized by a X-ray powder diagram with the characteristic values d=9.87 Å; 11.00 Å; 13.31 Å; 13.47 Å; 15.15 Å; 15.35 Å; 16.30 Å; 18.06 Å; 19.80 Å; 19.93 Å; 20.26 Å; 20.77 Å; 21.33 Å; 23.54 Å; 24.02 Å; 24.64 Å; 25.08 Å; 25.85 Å; 27.02 Å; 27.68 Å; 27.93 Å; 29.50 Å; and 29.86 Å; inter alia.

In another embodiment, the present invention relates to a 1,2-propanediol solvate of tiotropium bromide. In another aspect the present invention relates to a method of preparing the new crystalline 1,2-propanediol solvate of tiotropium bromide which is explained by way of example in the experimental section that follows.

The invention relates to this crystalline 1,2-propanediol solvate of tiotropium bromide which is characterized by a X-ray powder diagram with the characteristic values d=8.89 Å; 7.97 Å; 6.59 Å; 5.77 Å; 5.43 Å; 4.90 Å; 4.44 Å; 4.17 Å; 3.85 Å; 3.73 Å; 3.60 Å; 3.55 Å; 3.42 Å; 3.30 Å; 3.20 Å; and 2.96 Å; inter alia.

In another embodiment, the present invention relates to a pyridine solvate of tiotropium bromide. In another aspect the present invention relates to a method of preparing the new crystalline pyridine solvate of tiotropium bromide which is explained by way of example in the experimental section that follows.

The invention relates to this crystalline pyridine solvate of tiotropium bromide which is characterized by a X-ray powder diagram with the characteristic values d=13.06 Å; 8.89 Å; 7.88 Å; 6.57 Å; 5.76 Å; 5.40 Å; 4.89 Å; 4.45 Å; 4.16 Å; 3.72 Å; 3.55 Å; 3.43 Å; 3.29 Å; 3.19 Å; and 2.95 Å; inter alia.

In another embodiment, the present invention relates to a tert.-butanol solvate of tiotropium bromide. In another aspect the present invention relates to a method of preparing the new crystalline tert.-butanol solvate of tiotropium bromide which is explained by way of example in the experimental section that follows.

The invention relates to this crystalline tert.-butanol solvate of tiotropium bromide which is characterized by a X-ray powder diagram with the characteristic values d=13.13 Å; 8.81 Å; 7.98 Å; 6.57 Å; 5.76 Å; 5.41 Å; 4.89 Å; 4.44 Å; 4.23 Å; 4.14 Å; 3.73 Å; 3.56 Å; 3.42 Å; 3.29 Å; 3.19 Å; and 2.95 Å; inter alia.

In another embodiment, the present invention relates to a tetrahydrofuran (=THF) solvate of tiotropium bromide. In another aspect the present invention relates to a method of preparing the new crystalline THF solvate of tiotropium bromide which is explained by way of example in the experimental section that follows.

The invention relates to this crystalline THF solvate of tiotropium bromide which is characterized by a X-ray powder diagram with the characteristic values d=8.69 Å; 7.84 Å; 6.47 Å; 5.92 Å; 5.70 Å; 5.37 Å; 4.85 Å; 4.41 Å; 4.34 Å; 4.19 Å; 4.09 Å; 3.81 Å; 3.69 Å; 3.58 Å; 3.52 Å; 3.40 Å; 3.27 Å; 3.18 Å; and 2.94 Å; inter alia.

In another embodiment, the present invention relates to a tetrahydropyran (=THP) solvate of tiotropium bromide. In another aspect the present invention relates to a method of preparing the new crystalline THP solvate of tiotropium bromide which is explained by way of example in the experimental section that follows.

The invention relates to this crystalline THP solvate of tiotropium bromide which is characterized by a X-ray powder diagram with the characteristic values d=8.94 Å; 7.97 Å; 6.54 Å; 5.75 Å; 5.35 Å; 4.89 Å; 4.44 Å; 4.23 Å; 4.13 Å; 3.89 Å; 3.79 Å; 3.65 Å; 3.60 Å; 3.53 Å; 3.43 Å; 3.24 Å; 3.17 Å; and 2.98 Å; inter alia.

The present invention also relates to the use of the crystalline tiotropium bromide forms according to the invention for preparing a pharmaceutical composition for the treatment of respiratory complaints, particularly for the treatment of COPD and/or asthma.

The present invention also relates to methods for the preparation of the crystalline tiotropium bromide forms according to the inventions.

In another aspect the present invention relates to a method of preparing the new crystalline form of anhydrous tiotropium bromide characterized in that crystalline tiotropium bromide monohydrate (as known from WO 02/30928) is dissolved in a suitable solvent, preferably a solvent mixture comprising N,N-dimethylacetamide, more preferably a solvent mixture comprising dimethylacetamide and water, heated for 10-60 minutes to a temperature in the range of about 30-70° C., preferably 40-60° C., which, after cooling to a temperature below 15° C., preferably below 10° C., leads to the crystalline anhydrate, precipitating from the mixture. Another aspect of the invention is directed to the use of tiotropium bromide monohydrate as a starting material for the preparation of the crystalline tiotropium bromide anhydrate according to the invention.

In another aspect the present invention relates to a method of preparing the new crystalline methanol solvate of tiotropium bromide characterized in that crystalline tiotropium bromide monohydrate (as known from WO 02/30928) is dried at a temperature of 60-90° C., preferably 70-85° C. for a period of about 10 to 60 min, preferably 20-40 min, thereafter dissolved in a methanol containing solvent, preferably in a solvent mixture comprising methanol and acetone and subsequently cooled to a temperature below 0° C., preferably to a temperature in the range of −30 to −10° C. for at least 10 h, preferably for 12-20 h, the crystals of the methanol solvate thus obtained being isolated and dried. Another aspect of the invention is directed to the use of tiotropium bromide monohydrate as a starting material for the preparation of the crystalline methanol solvate of tiotropium bromide according to the invention.

In another aspect the present invention relates to a method of preparing the new crystalline ethanol solvate of tiotropium bromide characterized in that crystalline tiotropium bromide monohydrate (as known from WO 02/30928) is dried at a temperature of 60-90° C., preferably 70-85° C. for a period of about 10 to 60 min, preferably 20-40 min, thereafter dissolved in an ethanol containing solvent, preferably in a solvent mixture comprising ethanol and acetone and subsequently cooled to a temperature below 0° C., preferably to a temperature in the range of −30 to −10° C. for at least 10 h, preferably for 12-20 h, the crystals thus obtained being isolated and dried. Another aspect of the invention is directed to the use of tiotropium bromide monohydrate as a starting material for the preparation of the crystalline ethanol solvate of tiotropium bromide according to the invention.

In another aspect the present invention relates to a method of preparing the new crystalline isopropanol solvate of tiotropium bromide characterized in that crystalline tiotropium bromide monohydrate (as known from WO 02/30928) is dried at a temperature of 60-90° C., preferably 70-85° C. for a period of about 10 to 60 min, preferably 20-40 min, thereafter dissolved in a methanol containing solvent, preferably in pure methanol, the solution thus obtained being added to an isopropanol containing solvent, preferably to pure isopropanol, and subsequently cooled to a temperature below 15° C., preferably to a temperature in the range of 0 to 5° C. for at least 8 h, preferably for 10-16 h, the crystals thus obtained being isolated and dried. Another aspect of the invention is directed to the use of tiotropium bromide monohydrate as a starting material for the preparation of the crystalline isopropanol solvate of tiotropium bromide according to the invention.

In another aspect the present invention relates to a method of preparing the new crystalline n-butanol solvate of tiotropium bromide characterized in that crystalline tiotropium bromide monohydrate (as known from WO 02/30928) is dried at a temperature of 60-90° C., preferably 70-85° C. for a period of about 10 to 60 min, preferably 20-40 min, thereafter dissolved in a methanol containing solvent, preferably in pure methanol, the solution thus obtained being added to a n-butanol containing solvent, preferably to pure n-butanol and subsequently cooled to a temperature below 15° C., preferably to a temperature in the range of 0 to 5° C. for at least 8 h, preferably for 10-16 h, the crystals thus obtained being isolated and dried. Another aspect of the invention is directed to the use of tiotropium bromide monohydrate as a starting material for the preparation of the crystalline n-butanol solvate of tiotropium bromide according to the invention.

In another aspect the present invention relates to a method of preparing the new crystalline THF solvate of tiotropium bromide characterized in that crystalline tiotropium bromide monohydrate (as known from WO 02/30928) is dried at a temperature of 60-90° C., preferably 70-85° C. for a period of about 10 to 60 min, preferably 20-40 min, thereafter dissolved in a methanol containing solvent, preferably in pure methanol, the solution thus obtained being added to a THF containing solvent, preferably to pure THF and subsequently cooled to a temperature below 15° C., preferably to a temperature in the range of 0 to 5° C. for at least 8 h, preferably for 10-16 h, the crystals thus obtained being isolated and dried. Another aspect of the invention is directed to the use of tiotropium bromide monohydrate as a starting material for the preparation of the crystalline THF solvate of tiotropium bromide according to the invention.

In another aspect the present invention relates to a method of preparing the new crystalline dioxane solvate of tiotropium bromide characterized in that crystalline tiotropium bromide monohydrate (as known from WO 02/30928) is dried at a temperature of 60-90° C., preferably 70-85° C. for a period of about 10 to 60 min, preferably 20-40 min, thereafter dissolved in a methanol containing solvent, preferably in pure methanol, the solution thus obtained being added to a dioxane containing solvent, preferably to pure dioxane and subsequently cooled to a temperature below 15° C., preferably to a temperature in the range of 0 to 5° C. for ate least 8 h, preferably for 10-16 h, the crystals thus obtained being isolated and dried. Another aspect of the invention is directed to the use of tiotropium bromide monohydrate as a starting material for the preparation of the crystalline dioxane solvate of tiotropium bromide according to the invention.

In another aspect the present invention relates to a method of preparing the new crystalline 1,2-propandiol solvate of tiotropium bromide characterized in that crystalline tiotropium bromide monohydrate (as known from WO 02/30928) is dried at a temperature of 60-90° C., preferably 70-85° C. for a period of about 10 to 60 min, preferably 20-40 min, thereafter dissolved in a 1,2-propandiol containing solvent, preferably in pure 1,2-propandiol, the solution thus obtained being held at a temperature in the range of 30-70° C., preferably 40-60° C. for a period of about 20-90 min, preferably 30-70 min, optionally filtered and subsequently cooled to a temperature below 15° C., preferably to a temperature in the range of 0 to 10° C. for at least 12 h, preferably for 18-30 h, the crystals thus obtained being isolated and dried. Another aspect of the invention is directed to the use of tiotropium bromide monohydrate as a starting material for the preparation of the crystalline 1,2-propandiol solvate of tiotropium bromide according to the invention.

In another aspect the present invention relates to a method of preparing the new crystalline anisol solvate of tiotropium bromide characterized in that crystalline tiotropium bromide monohydrate (as known from WO 02/30928) is dried at a temperature of 60-90° C., preferably 70-85° C. for a period of about 10 to 60 min, preferably 20-40 min, thereafter dissolved in a anisol containing solvent, preferably in pure anisol, the solution thus obtained being held at a temperature in the range of 30-70° C., preferably 40-60° C. for a period of about 20-90 min, preferably 30-70 min, optionally filtered and subsequently cooled to a temperature below 15° C., preferably to a temperature in the range of 0 to 10° C. for at least 12 h, preferably for 18-30 h, the crystals thus obtained being isolated and dried. Another aspect of the invention is directed to the use of tiotropium bromide monohydrate as a starting material for the preparation of the crystalline anisol solvate of tiotropium bromide according to the invention.

In another aspect the present invention relates to a method of preparing the new crystalline THP solvate of tiotropium bromide characterized in that crystalline tiotropium bromide monohydrate (as known from WO 02/30928) is dried at a temperature of 60-90° C., preferably 70-85° C. for a period of about 10 to 60 min, preferably 20-40 min, thereafter dissolved in a THP containing solvent, preferably in pure THP, the solution thus obtained being held at a temperature in the range of 30-70° C., preferably 40-60° C. for a period of about 20-90 min, preferably 30-70 min, optionally filtered and subsequently cooled to a temperature below 15° C., preferably to a temperature in the range of 0 to 10° C. for at least 12 h, preferably for 18-30 h, the crystals thus obtained being isolated and dried. Another aspect of the invention is directed to the use of tiotropium bromide monohydrate as a starting material for the preparation of the crystalline THP solvate of tiotropium bromide according to the invention.

In another aspect the present invention relates to a method of preparing the new crystalline DMF solvate of tiotropium bromide characterized in that crystalline tiotropium bromide monohydrate (as known from WO 02/30928) is dried at a temperature of 60-90° C., preferably 70-85° C. for a period of about 10 to 60 min, preferably 20-40 min, thereafter suspended in a DMF containing solvent, preferably in pure DMF, to the solution thus obtained being added an antisolvent, preferably methylene chloride, the crystals thus obtained being isolated and dried. Another aspect of the invention is directed to the use of tiotropium bromide monohydrate as a starting material for the preparation of the crystalline DMF solvate of tiotropium bromide according to the invention.

In another aspect the present invention relates to a method of preparing the new crystalline DMA solvate of tiotropium bromide characterized in that crystalline tiotropium bromide monohydrate (as known from WO 02/30928) is dried at a temperature of 60-90° C., preferably 70-85° C. for a period of about 10 to 60 min, preferably 20-40 min, thereafter suspended in a DMA containing solvent, preferably in pure DMA, to the solution thus obtained being added an antisolvent, preferably methylene chloride, the crystals thus obtained being isolated and dried. Another aspect of the invention is directed to the use of tiotropium bromide monohydrate as a starting material for the preparation of the crystalline DMA solvate of tiotropium bromide according to the invention.

In another aspect the present invention relates to a method of preparing the new crystalline THF solvate of tiotropium bromide characterized in that crystalline tiotropium bromide monohydrate (as known from WO 02/30928) is dissolved in an acetone containing solvent, preferably in a solvent mixture comprising acetone and water, the solvent being slowly evaporated and the remaining solid being treated with a THF containing solvent, preferably with a solvent comprising THF and water, the solution thus obtained being held at a temperature in the range of 30-70° C., preferably 40-60° C. for a period of about 10-60 min, preferably 20-40 min and subsequently cooled to a temperature below 15° C., preferably to a temperature in the range of 0 to 10° C. for at least 12 h, preferably for 18-30 h, the crystals thus obtained being isolated and dried. Another aspect of the invention is directed to the use of tiotropium bromide monohydrate as a starting material for the preparation of the crystalline THF solvate of tiotropium bromide according to the invention.

In another aspect the present invention relates to a method of preparing the new crystalline tert.-butanol solvate of tiotropium bromide characterized in that crystalline tiotropium bromide monohydrate (as known from WO 02/30928) is dissolved in an acetone containing solvent, preferably in a solvent mixture comprising acetone and water, the solvent being slowly evaporated and the remaining solid being treated with a tert.-butanol containing solvent, preferably with a solvent comprising tert.-butanol and water, the solution thus obtained being held at a temperature in the range of 30-70° C., preferably 40-60° C. for a period of about 10-60 min, preferably 20-40 min and subsequently cooled to a temperature below 15° C., preferably to a temperature in the range of 0 to 10° C. for at least 12 h, preferably for 18-30 h, the crystals thus obtained being isolated and dried. Another aspect of the invention is directed to the use of tiotropium bromide monohydrate as a starting material for the preparation of the crystalline tert.-butanol solvate of tiotropium bromide according to the invention.

In another aspect the present invention relates to a method of preparing the new crystalline pyridine solvate of tiotropium bromide characterized in that crystalline tiotropium bromide monohydrate (as known from WO 02/30928) is dissolved in an acetone containing solvent, preferably in a solvent mixture comprising acetone and water, the solvent being slowly evaporated and the remaining solid being treated with a pyridine containing solvent, preferably with a solvent comprising pyridine and water, the solution thus obtained being held at a temperature in the range of 30-70° C., preferably 40-60° C. for a period of about 10-60 min, preferably 20-40 min and subsequently cooled to a temperature below 15° C., preferably to a temperature in the range of 0 to 10° C. for at least 12 h, preferably for 18-30 h, the crystals thus obtained being isolated and dried. Another aspect of the invention is directed to the use of tiotropium bromide monohydrate as a starting material for the preparation of the crystalline pyridine solvate of tiotropium bromide according to the invention.

EXAMPLES

The Examples that follow serve to illustrate the present invention still further, without restricting the scope of the invention to the embodiments by way of example that follow.

Examples of Synthesis According to the Invention

Example 1

Crystalline Tiotropium Bromide Anhydrate 600 mg of crystalline tiotropium bromide monohydrate (according to WO 02/30928) are dissolved in 10 ml of a mixture of N,N-dimethylacetamide:water=1:1. The solution is stirred at 50° C. for 30 minutes. Afterwards the solvent is slowly evaporated at room temperature under vacuum (ca. 1 kPa). After approx. 24 h first crystals of crystalline anhydrous tiotropium bromide are formed which are obtained by filtration and dried at ambient conditions.

Example 2

Crystalline Methanol Solvate of Tiotropium Bromide 1.0 g of tiotropium bromide monohydrate (according to WO 02/30928) are dried at 80° C. for 30 minutes under vacuum. The anhydrous form obtained by this procedure is dissolved afterwards in 10 ml of a mixture of methanol/acetone=2:1 under stirring. The solution is stored in a refrigerator at −20° C. for 16 h. Upon slowly warming up the solution to room temperature under stirring tiotropium bromide methanol solvate crystallizes. The crystals are filtered off and dried at ambient conditions.

Example 3

Crystalline Ethanol Solvate of Tiotropium Bromide 1.0 g of tiotropium bromide monohydrate (according to WO 02/30928) are dried at 80° C. for 30 minutes under vacuum. The anhydrous form obtained by this procedure is dissolved afterwards in 10 ml of a mixture of ethanol/acetone=2:1 under stirring. The solution is stored in a refrigerator at −20° C. for 16 h. Upon slowly warming up the solution to room temperature under stirring tiotropium bromide ethanol solvate crystallizes. The crystals are filtered off and dried at ambient conditions.

Example 4

Crystalline Isopropanol Solvate of Tiotropium Bromide 2.0 g of tiotropium bromide monohydrate (according to WO 02/30928) are dried at 80° C. for 30 minutes under vacuum. The anhydrous form obtained by this procedure is dissolved afterwards in 50 ml of methanol under stirring. This methanolic solution of tiotropium bromide is slowly added at room temperature to 50 ml of isopropanol under stirring. The mixture is stirred for another 30 minutes at room temperature and than stored over night in the refrigerator at 4° C. The obtained crystals are filtered of and dried under ambient conditions.

Example 5

Crystalline N-Butanol Solvate of Tiotropium Bromide 2.0 g of tiotropium bromide monohydrate (according to WO 02/30928) are dried at 80° C. for 30 minutes under vacuum. The anhydrous form obtained by this procedure is dissolved afterwards in 50 ml of methanol under stirring. This methanolic solution of tiotropium bromide is slowly added at room temperature to 50 ml of n-butanol under stirring. The mixture is stirred for another 30 minutes at room temperature and than stored over night in the refrigerator at 4° C. The obtained crystals are filtered of and dried under ambient conditions.

Example 6

Crystalline THF Solvate of Tiotropium Bromide 2.0 g of tiotropium bromide monohydrate (according to WO 02/30928) are dried at 80° C. for 30 minutes under vacuum. The anhydrous form obtained by this procedure is dissolved afterwards in 50 ml of methanol under stirring. This methanolic solution of tiotropium bromide is slowly added at room temperature to 50 ml of tetrahydrofuran under stirring. The mixture is stirred for another 30 minutes at room temperature and than stored over night in the refrigerator at 4° C. The obtained crystals are filtered of and dried under ambient conditions.

Example 7

Crystalline 1,4-dioxane Solvate of Tiotropium Bromide 2.0 g of tiotropium bromide monohydrate (according to WO 02/30928) are dried at 80° C. for 30 minutes under vacuum. The anhydrous form obtained by this procedure is dissolved afterwards in 50 ml of methanol under stirring. This methanolic solution of tiotropium bromide is slowly added at room temperature to 50 ml of dioxane under stirring. The mixture is stirred for another 30 minutes at room temperature and than stored over night in the refrigerator at 4° C. The obtained crystals are filtered of and dried under ambient conditions.

Example 8

Crystalline 1,2-propanediol Solvate of Tiotropium Bromide 2.0 g of tiotropium bromide monohydrate (according to WO 02/30828) are dried at 80° C. for 30 minutes under vacuum. The anhydrous form obtained by this procedure is suspended in 10 ml of 1,2-propanediol at 50° C. for 20 minutes and afterwards filtered to obtain a saturated solution of tiotropium bromide in 1,2-propanediol. The concentration was measured by HPLC and determined to be approx. 100 mg/ml of tiotropium bromide in 1,2-propandiol. After filtration of the slurries at 50° C., a small portion was transferred to a 1.8 ml glass vial and placed into an apparatus to control temperature. The solution was kept for another 30 minutes at 50° C. and afterwards cooled with a cooling rate of 30° C./h to a final temperature of 5° C. At this temperature the solid remained in the solution for a hold time of 24 h. After the cooling crystallization step the dry solids were obtained by filtration and dried under ambient conditions.

Example 9

Crystalline Anisol Solvate of Tiotropium Bromide 1.0 g of tiotropium bromide monohydrate (according to WO 02/30928) are suspended in 5 ml of an anisole (=methoxy benzene)/water mixture with a ratio of 60:40 at 50° C. for 20 minutes and afterwards filtered to obtain a saturated solution of tiotropium bromide in this solvent mixture. The concentration was measured by HPLC and determined to be approx. 90 mg/ml of tiotropium bromide in anisol/water=60:40. After filtration of the slurries at 50° C., a small portion was transferred to a 1.8 ml glass vial and placed into an apparatus to control temperature. The solution was kept for another 30 minutes at 50° C. and afterwards cooled with a cooling rate of 30° C./h to a final temperature of 5° C. At this temperature the solid remained in the solution for a hold time of 24 h. After the cooling crystallization step the dry solids were obtained by filtration and dried under ambient conditions.

Example 10

Crystalline THP Solvate of Tiotropium Bromide 1.0 g of tiotropium bromide monohydrate (according to WO 02/30928) are suspended in 5 ml of THP/water mixture with a ratio of 60:40 at 50° C. for 20 minutes and afterwards filtered to obtain a saturated solution of tiotropium bromide in this solvent mixture. The concentration was measured by HPLC and determined to be approx. 35 mg/ml of tiotropium bromide in THP/water=60:40. After filtration of the slurries at 50° C., a small portion was transferred to a 1.8 ml glass vial and placed into an apparatus to control temperature. The solution was kept for another 30 minutes at 50° C. and afterwards cooled with a cooling rate of 30° C./h to a final temperature of 5° C. At this temperature the solid remained in the solution for a hold time of 24 h. After the cooling crystallization step the dry solids were obtained by filtration and dried under ambient conditions.

Example 11

Crystalline DMF Solvate of Tiotropium Bromide 1.0 g of tiotropium bromide monohydrate (according to WO 02/30928) are dried at 80° C. for 30 minutes under vacuum. The anhydrous form obtained by this procedure is suspended in 10 ml of DMf at room temperature for 2 hours and afterwards filtered to obtain a saturated solution of tiotropium bromide in DMA. The concentration was measured by HPLC and determined to be approx. 75 mg/ml of tiotropium bromide in DMF. After filtration of the slurries at room temperature, a small portion was transferred to a 1.8 ml glass vial. Dichloromethane was added as antisolvent in a ratio of solvent antisolvent=1:2. The precipitated solid was obtained by filtration and dried under ambient conditions.

Example 12

Crystalline DMA Solvate of Tiotropium Bromide 1.0 g of tiotropium bromide monohydrate (according to WO 02/30928) are dried at 80° C. for 30 minutes under vacuum. The anhydrous form obtained by this procedure is suspended in 10 ml of DMA at room temperature for 2 hours and afterwards filtered to obtain a saturated solution of tiotropium bromide in DMA. The concentration was measured by HPLC and determined to be approx. 40 mg/ml of tiotropium bromide in DMA. After filtration of the slurries at room temperature, a small portion was transferred to a 1.8 ml glass vial. Dichloromethane was added as antisolvent in a ratio of solvent antisolvent=1:2. The precipitated solid was obtained by filtration and dried under ambient conditions.

Example 13

Crystalline THF Solvate of Tiotropium Bromide 600 mg of crystalline tiotropium bromide (according to WO 02/30928) are dissolved in 10 ml of a mixture of acetone/water=80:20. 40 µl of this stock solution is transferred into one of the small vials of a 96 well plate. The plate containing the stock solution was placed in a vacuum chamber (1.3 kPa) at room temperature for 40 h. After the stock solvent was evaporated 40 µl of a mixture of THF/water=60:40 was added to this vial. The whole 96 well plate is sealed afterwards and heated up with a heating rate of 5° C./min to 50° C. at which the plate stays for an additional 30 minutes. Afterwards the plate is cooled with a cooling rate of 5° C./h to a final temperature of 5° C. At this temperature the plate remained for a hold time of 24 h. The plates are opened afterwards the solid is obtained by evaporation of the solvent at room temperature in a vacuum chamber (13 kPa).

Example 14

Crystalline tert.-butanol Solvate Of Tiotropium Bromide 600 mg of crystalline tiotropium bromide (according to WO 02/30928) are dissolved in 10 ml of a mixture of tert.-acetone/water=80:20. 40 µl of this stock solution is transferred into one of the small vials of a 96 well plate. The plate containing the stock solution was placed in a vacuum chamber (1.3 kPa) at room temperature for 40 h. After the stock solvent was evaporated 40 µl of a mixture of tert.-butanol/water=20:80 was added to this vial. The whole 96 well plate is sealed afterwards and heated up with a heating rate of 5° C./min to 50° C. at which the plate stays for an additional 30 minutes. Afterwards the plate is cooled with a cooling rate of 5° C./h to a final temperature of 5° C. At this temperature the plate remained for a hold time of 24 h. The plates are opened afterwards the solid is obtained by evaporation of the solvent at room temperature in a vacuum chamber (13 kPa).

Example 15

Crystalline Pyridine Solvate of Tiotropium Bromide 600 mg of crystalline tiotropium bromide (according to WO 02/30928) are dissolved in 10 ml of a mixture of acetone/water=80:20. 40 µl of this stock solution is transferred into one of the small vials of a 96 well plate. The plate containing the stock solution was placed in a vacuum chamber (1.3 kPa) at room temperature for 40 h. After the stock solvent was evaporated 40 µl of a mixture of pyridine/water=50:50 was added to this vial. The whole 96 well plate is sealed afterwards and heated up with a heating rate of 5° C./min to 50° C. at which the plate stays for an additional 30 minutes. Afterwards the plate is cooled with a cooling rate of 5° C./h to a final temperature of 5° C. At this temperature the plate remained for a hold time of 24 h. The plates are opened afterwards the solid is obtained by evaporation of the solvent at room temperature in a vacuum chamber (13 kPa).

Characterisation of the Tiotropium Bromide Forms According to the Invention

Methods:

Single Crystal X-Ray Diffraction

Suitable single crystal selected after the crystallization experiments, were glued to a glass fibre, which was mounted on an X-ray diffraction goniometer. X-ray diffraction data was collected for these crystals at a temperature of 233 K using KappaCCD system and MoKα radiation generated by a FR590 X-ray generator (Bruker Nonius, Delft, The Netherlands).

Unit-cell parameters and crystal structures were determined and refined using the software package maXus (Mackay et al., 1997). From the crystal structure the theoretical X-ray powder diffraction pattern were calculated using PowderCell for Windows version 2.3 (Kraus et al., 1999).

X-Ray Powder Diffraction

X-Ray powder diffraction patterns were obtained using Avantium's T2 high throughput XRPD set-up. The plates were mounted on a Bruker GADDS diffractometer that is equipped with a Hi-Star area detector. The XRPD platform is calibrated using Silver Behenate for the long d-spacings and Corundum for the short d-spacings.

The data collection was carried out at room temperature using monochromatic CuK$_\alpha$ radiation in the region of 2θ between 1.5 and 41.5°. The diffraction pattern of each well was collected in two 2theta ranges (1.5≦2θ≦19.5° for the 1st frame, and 21.5≦2θ≦41.5° for the second frame) with an exposure time between 90 and 180 s for each frame. No background subtraction or curve smoothing was applied to the XRPD patterns.

Characterization of Crystalline Tiotropium Bromide Anhydrate

The crystalline tiotropium bromide anhydrate crystallizes in an orthorhombic crystallographic system (see Table 1).

TABLE 1

Crystal and structure refinement data for form C.

| | |
|---|---|
| Empirical formula | $C_{19}H_{22}NO_4S_2^+ \cdot Br^-$ |
| Fw | 472.41 |
| T [K] | 293(2) |
| λ[Å] | 0.71073 |
| Crystal system | Orthorhombic |
| Space group | P bca |
| Unit cell dimensions | |
| a [Å] | a = 11.7420(4) |
| b [Å] | b = 17.7960(7) |
| c [Å] | c = 19.6280(11) |
| β [°] | |
| V [Å$^3$] | 4101.5(3) |
| Z | 8 |
| D$_m$ [g/cm$^3$] | 1.530 |
| F(000) | 1936 |
| Crystal size [mm$^3$] | 0.4 × 0.4 × 0.1 |
| θ range[°] | 2 → 27.5. |
| Reflections collected | 20542 |
| Independent reflections | 4648 [R$_{int}$ = 0.0442] |
| Data/restraints/parameters | 4648/0/350 |
| S | 1.038 |
| R [I > 2σ(I)] | R1 = 0.0445, wR2 = 0.0814 |
| R indices (all data) | R1 = 0.0732, wR2 = 0.0918 |
| Extinction coefficient | 0.0006(2) |

The tiotropium bromide anhydrate obtained by the above method is highly crystalline. It was investigated further by X-ray powder diffraction. The X-ray powder diagram obtained for the tiotropium bromide anhydrate according to the invention is shown in FIG. 1.

The following Table 2 lists the characteristic peaks and standardised intensities.

TABLE 2

X-ray powder reflections (up to 30° 2Θ) and intensities (normalized) of an anhydrous form of tiotropium bromide

| 2Θ [°] | d [Å] | I/I$_o$ [%] |
|---|---|---|
| 9.80 | 9.02 | 17 |
| 8.90 | 9.93 | 36 |
| 8.10 | 10.91 | 32 |
| 7.53 | 11.75 | 32 |
| 6.60 | 13.41 | 7 |
| 5.87 | 15.08 | 89 |
| 5.57 | 15.89 | 4 |
| 5.44 | 16.28 | 11 |
| 5.36 | 16.53 | 5 |
| 5.11 | 17.33 | 5 |
| 4.91 | 18.07 | 56 |
| 4.85 | 18.29 | 41 |
| 4.81 | 18.44 | 38 |
| 4.66 | 19.03 | 10 |
| 4.53 | 19.58 | 2 |
| 4.45 | 19.94 | 4 |
| 4.39 | 20.23 | 11 |
| 4.34 | 20.45 | 15 |
| 4.30 | 20.65 | 11 |
| 4.24 | 20.91 | 29 |
| 4.17 | 21.27 | 27 |
| 4.11 | 21.59 | 9 |
| 4.05 | 21.91 | 100 |
| 3.84 | 23.14 | 52 |
| 3.75 | 23.68 | 17 |
| 3.68 | 24.14 | 23 |
| 3.60 | 24.73 | 17 |
| 3.52 | 25.31 | 18 |
| 3.44 | 25.91 | 28 |
| 3.36 | 26.50 | 5 |
| 3.30 | 27.01 | 7 |
| 3.22 | 27.65 | 16 |
| 3.18 | 28.07 | 6 |
| 3.15 | 28.35 | 10 |
| 3.10 | 28.74 | 10 |
| 3.06 | 29.12 | 13 |
| 2.97 | 30.05 | 11 |

In the above Table the value "2 Θ[°]" represents the diffraction angle in degrees and the value "d$_{hkl}$[Å]" represents the specified lattice plane intervals in Å.

Characterization of Crystalline 1,4-dioxane Solvate of Tiotropium Bromide

The crystalline 1,4-dioxane solvate tiotropium bromide crystallizes in an monoclinic crystallographic system (see Table 3).

TABLE 3

| | |
|---|---|
| Empirical formula | 2 ($C_{19}H_{22}NO_4S_2^+ \cdot Br^-$)•C4H8O2 |
| Fw | 516.47 |
| T [K] | 293(2) |
| λ[Å] | 0.71073 |
| Crystal system | Monoclinic |
| Space group | P 2$_1$/c |
| Unit cell dimensions | |
| a [Å] | 13.6650(3) |
| b [Å] | 12.0420(3) |
| c [Å] | 13.7090(3) |
| β [°] | 103.8150(13) |
| V [Å$^3$] | 2190.61(9) |

TABLE 3-continued

| | |
|---|---|
| Z | 4 |
| $D_m$ [g/cm³] | 1.566 |
| F(000) | 1064 |
| θ range[°] | 1.5 → 29 |
| Reflections total | 15269 |
| Independent reflections | 5034 |
| | [$R_{int}$ = 0.043] |
| Data/restraints/parameters | 5034/0/285 |
| S | 1.039 |
| R [I > 2σ(I)] | R1 = 0.071, |
| | wR2 = 0.193 |
| R indices (all data) | R1 = 0.095, |
| | wR2 = 0.220 |

Figure 2:
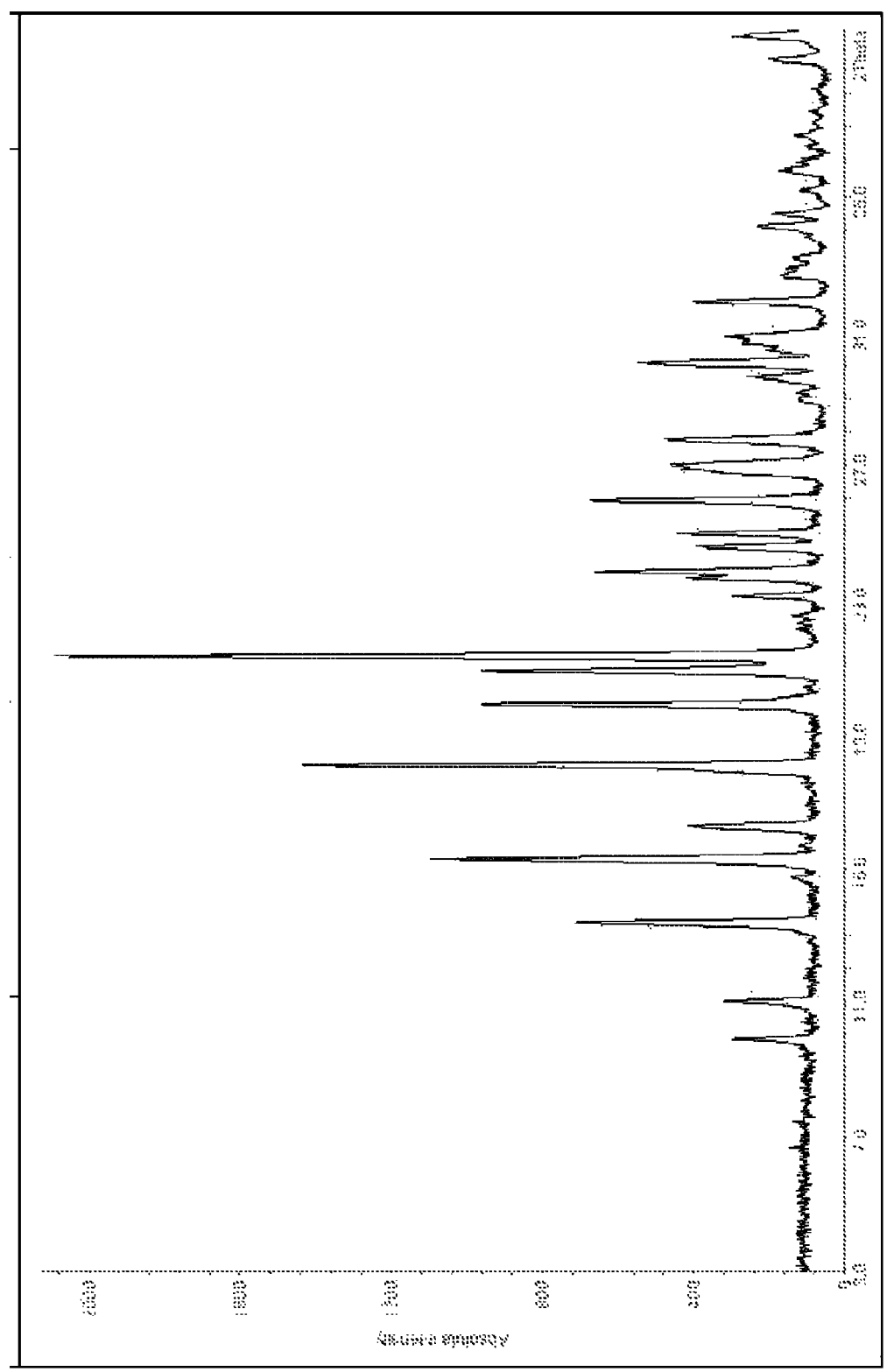
FIG. 2: X-ray powder diffraction of crystalline dioxane solvate of tiotropium bromide

The X-ray powder diagram obtained for the crystalline 1-4-dioxane solvate of tiotropium bromide is shown in FIG. 2. The following Table 4 lists the characteristic peaks and standardised intensities.

TABLE 4

X-ray powder reflections (up to 30° 2Θ) and intensities (normalized) of solvated form of tiotropium bromide containing dioxane with a stoichiometry of tiotropium bromide:dioxane close to 2:1

| 2Θ [°] | d [Å] | I/I$_o$ [%] |
|---|---|---|
| 8.91 | 9.92 | 11 |
| 8.02 | 11.03 | 12 |
| 6.61 | 13.38 | 32 |
| 6.01 | 14.72 | 3 |
| 5.80 | 15.27 | 49 |
| 5.45 | 16.24 | 17 |
| 4.90 | 18.09 | 68 |
| 4.46 | 19.88 | 46 |
| 4.25 | 20.88 | 44 |
| 4.16 | 21.33 | 100 |
| 3.94 | 22.54 | 3 |
| 3.84 | 23.12 | 11 |
| 3.76 | 23.64 | 18 |
| 3.73 | 23.85 | 29 |
| 3.62 | 24.58 | 16 |
| 3.56 | 24.99 | 18 |
| 3.43 | 25.95 | 31 |
| 3.30 | 26.98 | 20 |
| 3.21 | 27.77 | 21 |
| 3.07 | 29.05 | 2 |
| 3.01 | 29.64 | 9 |
| 2.97 | 30.05 | 24 |

Characterization of Crystalline Ethanol Solvate of Tiotropium Bromide

The crystalline ethanol solvate of tiotropium bromide crystallizes in an monoclinic crystallographic system (see Table 5).

TABLE 5

| | |
|---|---|
| Empirical formula | 2($C_{19}H_{22}NO_4S_2^+$•$Br^-$)•$C_2H_6O$ |
| Fw | 990.90 |
| T [K] | 120(2) |
| λ[Å] | 0.71073 |
| Crystal system | Monoclinic |
| Space group | P 2$_1$/c |
| Unit cell dimensions | |
| a [Å] | 13.5380(2) |
| b [Å] | 11.9830(2) |
| c [Å] | 26.9410(5) |
| β [°] | 105.1990(6) |
| V [Å³] | 4217.65(12) |
| Z | 8 |
| $D_m$ [g/cm³] | 1.561 |
| F(000) | 2040 |

TABLE 5-continued

| | |
|---|---|
| θ range[°] | 2.3 → 30.5 |
| Reflections total | 18368 |
| Independent reflections | 12282 |
| | [$R_{int}$ = 0.048] |
| Data/restraints/parameters | 12282/0/714 |
| S | 1.04 |
| R [I > 2σ(I)] | R1 = 0.0556 |
| | wR2 = 0.1239 |
| R indices (all data) | R1 = 0.0812 |
| | wR2 = 0.1395 |

Figure 3:
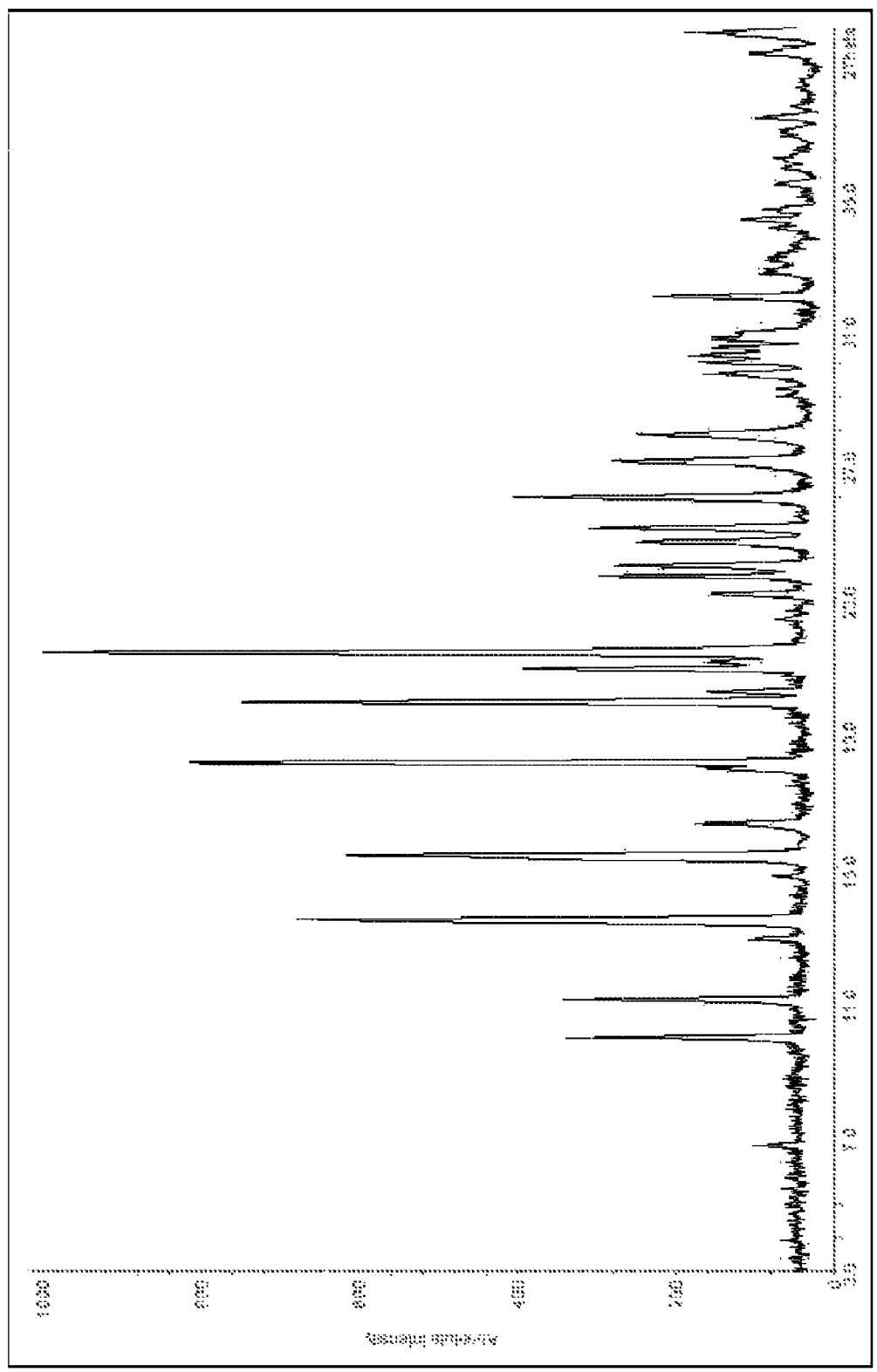
FIG. 3: X-ray powder diffraction of crystalline ethanol solvate of tiotropium bromide

The X-ray powder diagram obtained for the crystalline ethanol solvate of tiotropium bromide is shown in FIG. 3. The following Table 6 lists the characteristic peaks and standardised intensities.

TABLE 6

X-ray powder reflections (up to 30° 2Θ) and intensities (normalized) of a solvated form of tiotropium bromide containing ethanol with a stoichiometry of tiotropium bromide:ethanol close to 2:1

| 2Θ [°] | d [Å] | I/I$_o$ [%] |
|---|---|---|
| 13.16 | 6.71 | 6 |
| 8.91 | 9.92 | 29 |
| 8.00 | 11.05 | 30 |
| 6.88 | 12.86 | 7 |
| 6.60 | 13.41 | 63 |
| 6.02 | 14.71 | 3 |
| 5.77 | 15.34 | 61 |
| 5.43 | 16.31 | 13 |
| 4.94 | 17.93 | 13 |
| 4.89 | 18.12 | 85 |
| 4.46 | 19.91 | 76 |
| 4.39 | 20.22 | 12 |
| 4.25 | 20.90 | 38 |
| 4.21 | 21.11 | 11 |
| 4.15 | 21.39 | 100 |
| 3.97 | 22.39 | 3 |
| 3.84 | 23.13 | 12 |
| 3.76 | 23.65 | 27 |
| 3.71 | 23.96 | 25 |
| 3.61 | 24.67 | 23 |
| 3.55 | 25.08 | 28 |
| 3.42 | 26.00 | 37 |
| 3.29 | 27.07 | 25 |
| 3.20 | 27.85 | 21 |
| 3.08 | 29.00 | 4 |
| 3.06 | 29.20 | 4 |
| 3.01 | 29.66 | 13 |
| 2.97 | 30.02 | 14 |

Characterization of Crystalline Methanol Solvate of Tiotropium Bromide

The crystalline methanol solvate of tiotropium bromide crystallizes in an monoclinic crystallographic system (see Table 7).

TABLE 7

| | |
|---|---|
| Empirical formula | ($C_{19}H_{22}NO_4S_2^+$•$Br^-$)•$CH_4O$ |
| Fw | 500.43 |
| T [K] | 293(2) |
| λ[Å] | 0.71073 |
| Crystal system | Monoclinic |
| Space group | P 2$_1$/c |
| Unit cell dimensions | |
| a [Å] | 13.4420(2) |
| b [Å] | 37.0890(5) |
| c [Å] | 13.6290(2) |
| β [°] | 104.7050(10) |
| V [Å³] | 6572.18(16) |

TABLE 7-continued

| | |
|---|---|
| Z | 12 |
| $D_m$ [g/cm$^3$] | 1.529 |
| F(000) | 3120 |
| θ range[°] | 1.6 → 30.0 |
| Reflections total | 41043 |
| Independent reflections | 17392 |
| | [$R_{int}$ = 0.065] |
| Data/restraints/parameters | 17392/12/851 |
| S | 1.06 |
| R [I > 2σ(I)] | R1 = 0.0924 |
| | wR2 = 0.2766 |
| R indices (all data) | R1 = 0.1441 |
| | wR2 = 0.2364 |

Figure 4:
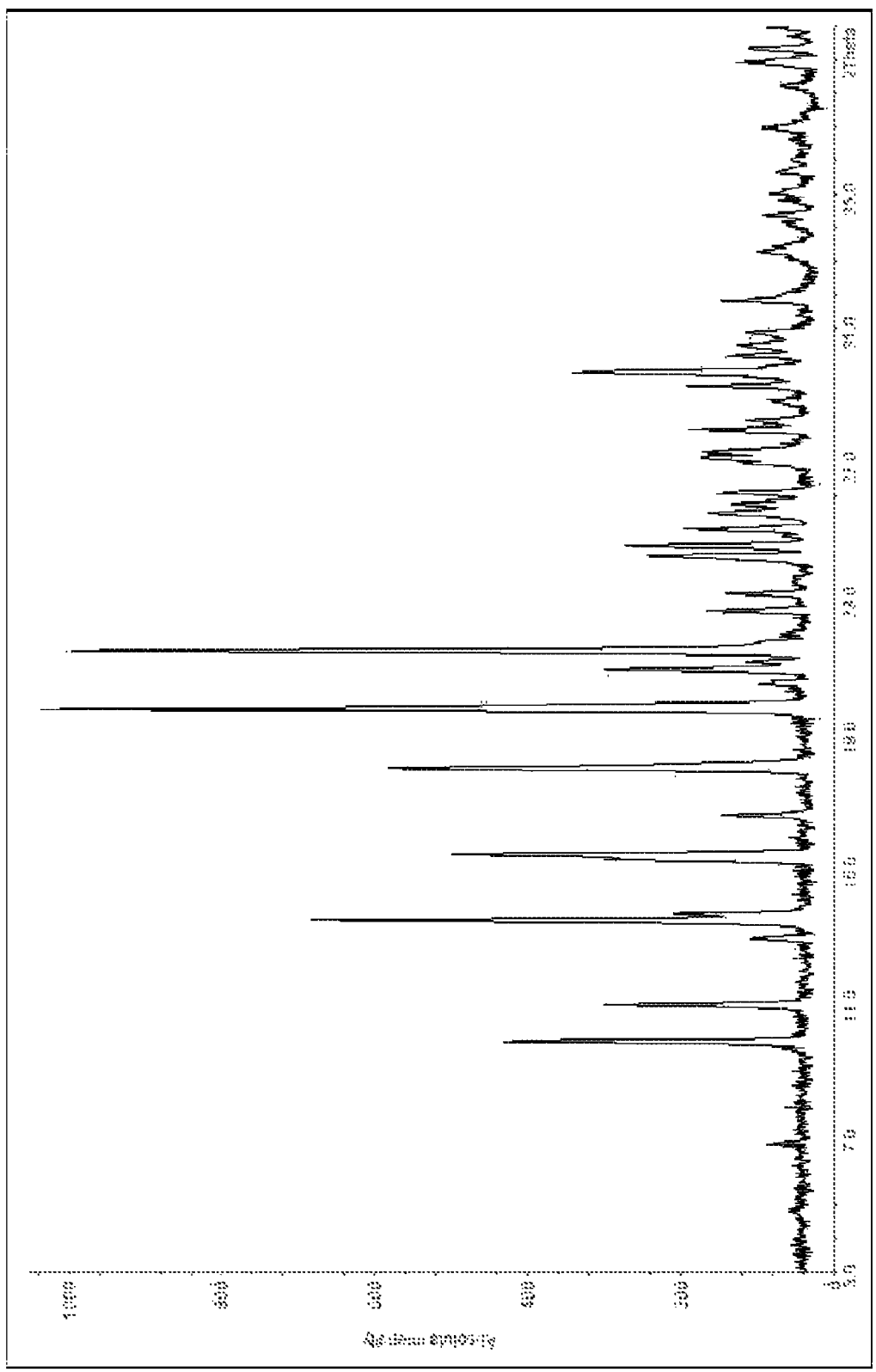
FIG. 4: X-ray powder diffraction of crystalline methanol solvate of tiotropium bromide

The X-ray powder diagram obtained for the crystalline methanol solvate of tiotropium bromide is shown in FIG. 4. The following Table 8 lists the characteristic peaks and standardised intensities.

TABLE 8

X-ray powder reflections (up to 30° 2Θ) and intensities (normalized) of a solvated form of tiotropium bromide containing methanol with a stoichiometry of tiotropium bromide:methanol close to 1:1

| 2Θ [°] | d [Å] | I/I$_o$ [%] |
|---|---|---|
| 13.00 | 6.79 | 5 |
| 8.98 | 9.84 | 38 |
| 8.09 | 10.93 | 24 |
| 6.86 | 12.89 | 7 |
| 6.59 | 13.43 | 60 |
| 6.50 | 13.61 | 14 |
| 5.81 | 15.25 | 26 |
| 5.76 | 15.38 | 43 |
| 5.35 | 16.55 | 11 |
| 4.94 | 17.94 | 53 |
| 4.50 | 19.70 | 100 |
| 4.34 | 20.45 | 6 |
| 4.25 | 20.88 | 26 |
| 4.21 | 21.11 | 8 |
| 4.14 | 21.44 | 92 |
| 3.93 | 22.63 | 12 |
| 3.84 | 23.14 | 10 |
| 3.67 | 24.25 | 20 |
| 3.62 | 24.55 | 23 |
| 3.55 | 25.05 | 13 |
| 3.49 | 25.52 | 12 |
| 3.45 | 25.78 | 10 |
| 3.41 | 26.12 | 11 |
| 3.30 | 27.01 | 9 |
| 3.28 | 27.17 | 14 |
| 3.26 | 27.33 | 13 |
| 3.18 | 27.99 | 15 |
| 3.15 | 28.27 | 8 |
| 3.09 | 28.85 | 5 |
| 3.05 | 29.30 | 16 |
| 3.01 | 29.71 | 30 |

Characterization of Crystalline Anisol Solvate of Tiotropium Bromide

Figure 5:
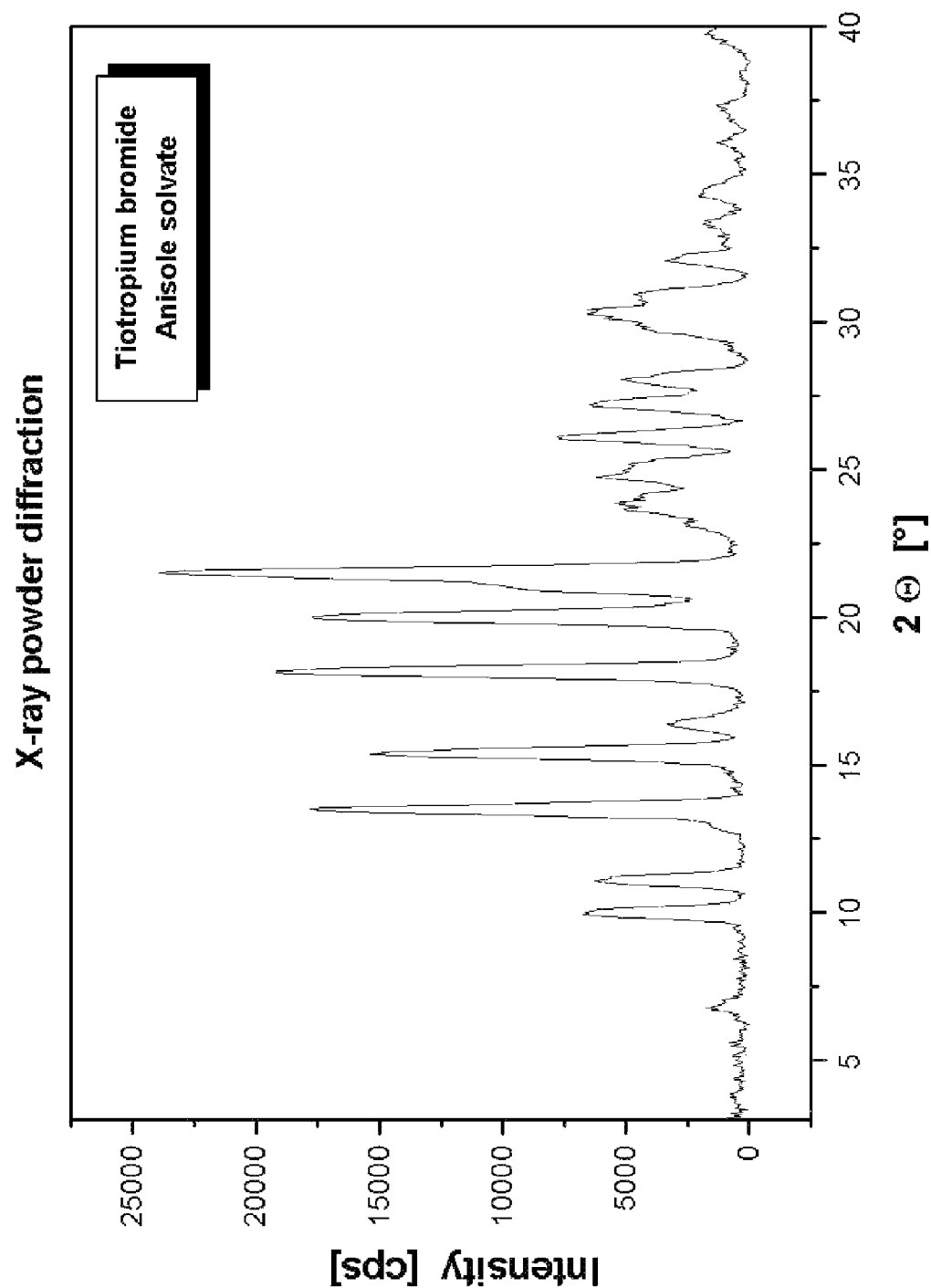
FIG. 5: X-ray powder diffraction of crystalline anisol solvate of tiotropium bromide

The X-ray powder diagram obtained for the crystalline anisol solvate of tiotropium bromide is shown in FIG. 5. The following Table 9 lists the characteristic peaks and standardised intensities.

TABLE 9

X-ray powder reflections (up to 30° 2Θ) and intensities (normalized) of solvated form of tiotropium bromide containing anisol

| 2Θ [°] | d [Å] | I/I$_o$ [%] |
|---|---|---|
| 6.80 | 12.99 | 7 |
| 10.00 | 8.84 | 28 |
| 11.11 | 7.96 | 26 |
| 12.93 | 6.84 | 6 |
| 13.51 | 6.55 | 75 |
| 15.38 | 5.76 | 64 |
| 16.40 | 5.40 | 13 |
| 18.16 | 4.88 | 80 |
| 20.01 | 4.43 | 73 |
| 21.07 | 4.21 | 42 |
| 21.47 | 4.14 | 100 |
| 23.85 | 3.73 | 22 |
| 24.88 | 3.58 | 23 |
| 26.11 | 3.41 | 32 |
| 27.23 | 3.27 | 27 |
| 28.02 | 3.18 | 21 |
| 29.79 | 3.00 | 18 |
| 30.29 | 2.95 | 27 |

Characterization of Crystalline N-Butanol Solvate of Tiotropium Bromide

Figure 6:
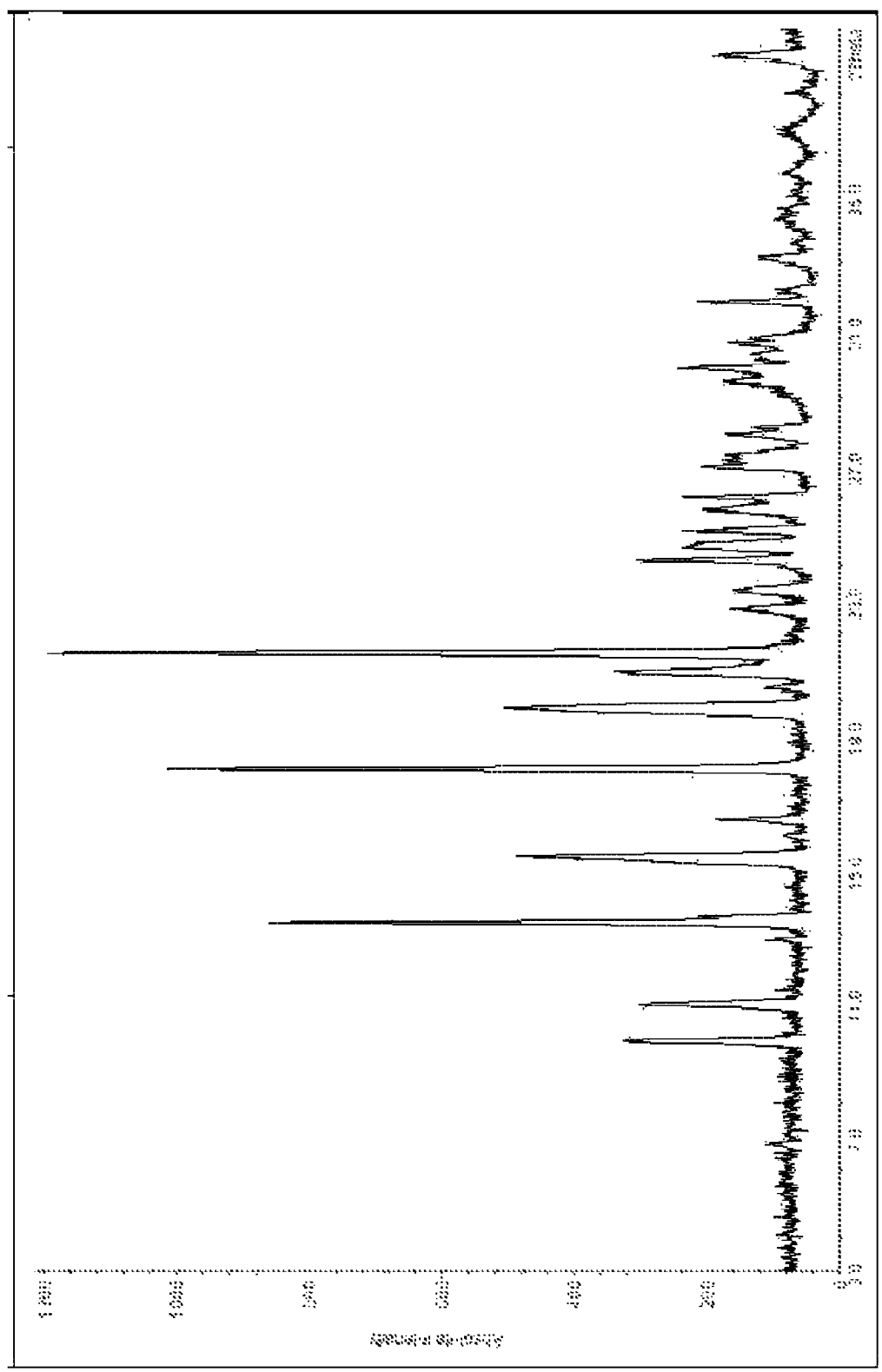
FIG. 6: X-ray powder diffraction of crystalline n-butanol solvate of tiotropium bromide

The X-ray powder diagram obtained for the crystalline n-butanol solvate of tiotropium bromide is shown in FIG. 6. The following Table 10 lists the characteristic peaks and standardised intensities.

TABLE 10

X-ray powder reflections (up to 30° 2Θ) and intensities (normalized) of a solvated form of tiotropium bromide containing n-butanol with a stoichiometry of tiotropium bromide:n-butanol close to 2:1

| 2Θ [°] | d [Å] | I/I$_o$ [%] |
|---|---|---|
| 13.08 | 6.75 | 4 |
| 8.99 | 9.83 | 21 |
| 8.09 | 10.93 | 21 |
| 6.89 | 12.84 | 5 |
| 6.61 | 13.38 | 70 |
| 6.53 | 13.54 | 13 |
| 5.77 | 15.34 | 37 |
| 5.38 | 16.46 | 11 |
| 4.94 | 17.95 | 85 |
| 4.49 | 19.77 | 38 |
| 4.36 | 20.36 | 3 |
| 4.26 | 20.83 | 24 |
| 4.15 | 21.41 | 100 |
| 3.91 | 22.71 | 8 |
| 3.82 | 23.27 | 9 |
| 3.68 | 24.15 | 23 |
| 3.62 | 24.56 | 16 |
| 3.55 | 25.03 | 15 |
| 3.47 | 25.66 | 13 |
| 3.42 | 26.03 | 16 |
| 3.31 | 26.95 | 14 |
| 3.27 | 27.27 | 9 |
| 3.20 | 27.89 | 10 |
| 3.17 | 28.12 | 6 |
| 3.03 | 29.48 | 11 |
| 2.99 | 29.87 | 16 |

Characterization of Crystalline DMA Solvate of Tiotropium Bromide

Figure 7:
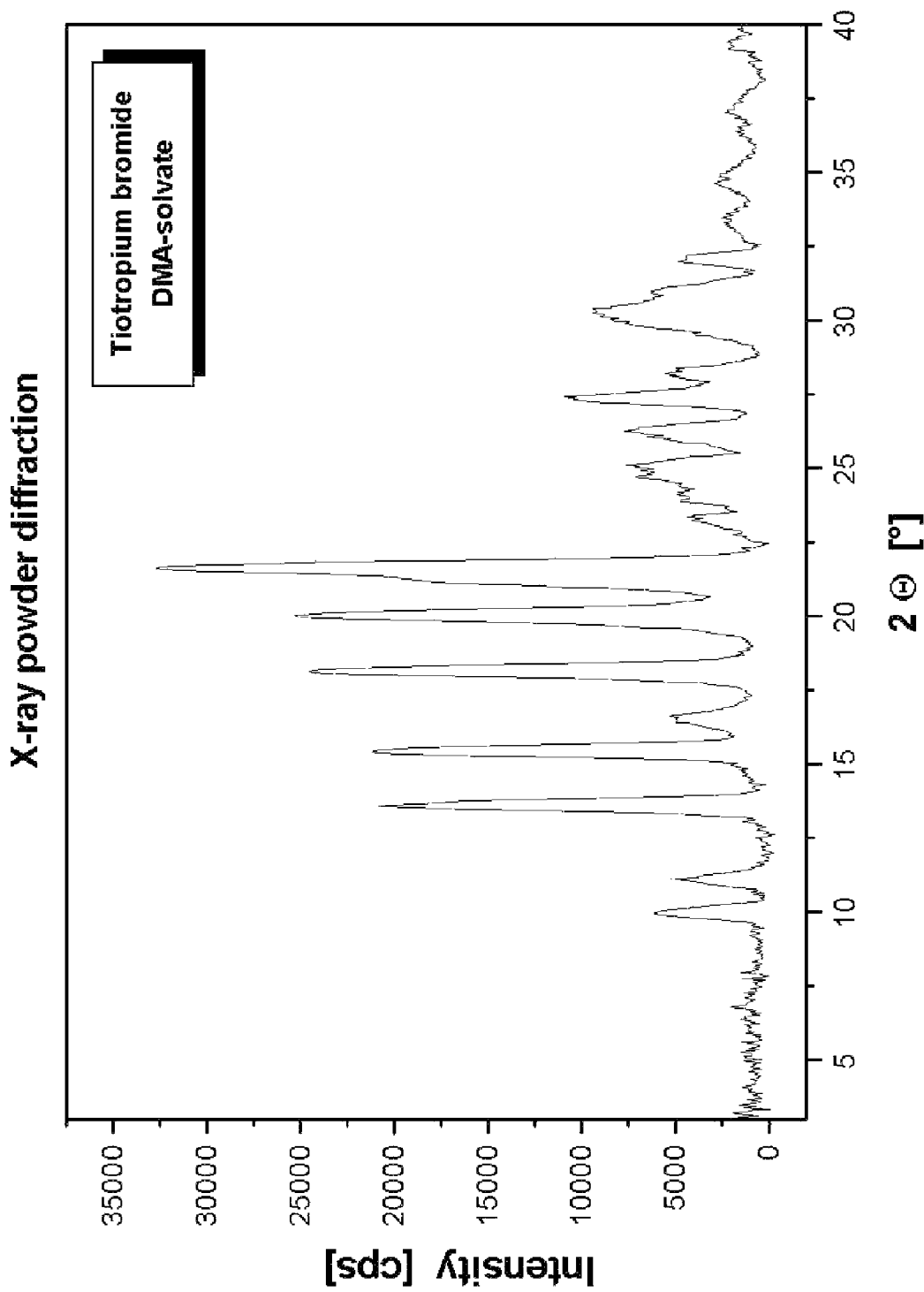
FIG. 7: X-ray powder diffraction of crystalline DMA solvate of tiotropium bromide

The X-ray powder diagram obtained for the crystalline DMA solvate of tiotropium bromide is shown in FIG. 7. The following Table 11 lists the characteristic peaks and standardised intensities.

TABLE 7

X-ray powder reflections (up to 30° 2Θ) and intensities
(normalized) of a solvated form of tiotropium bromide
containing N,N-dimethylacetamide (=DMA)

| 2Θ [°] | d [Å] | I/I$_o$ [%] |
|---|---|---|
| 9.98 | 8.86 | 16 |
| 11.20 | 7.89 | 17 |
| 13.62 | 6.50 | 62 |
| 15.46 | 5.73 | 49 |
| 16.50 | 5.37 | 13 |
| 18.14 | 4.89 | 67 |
| 20.06 | 4.42 | 77 |
| 21.26 | 4.18 | 62 |
| 21.65 | 4.10 | 100 |
| 23.22 | 3.83 | 9 |
| 23.90 | 3.72 | 23 |
| 25.03 | 3.55 | 21 |
| 26.23 | 3.39 | 22 |
| 27.38 | 3.25 | 34 |
| 28.26 | 3.16 | 15 |
| 30.24 | 2.95 | 32 |

Characterization of Crystalline DMF Solvate of Tiotropium Bromide

Figure 8:
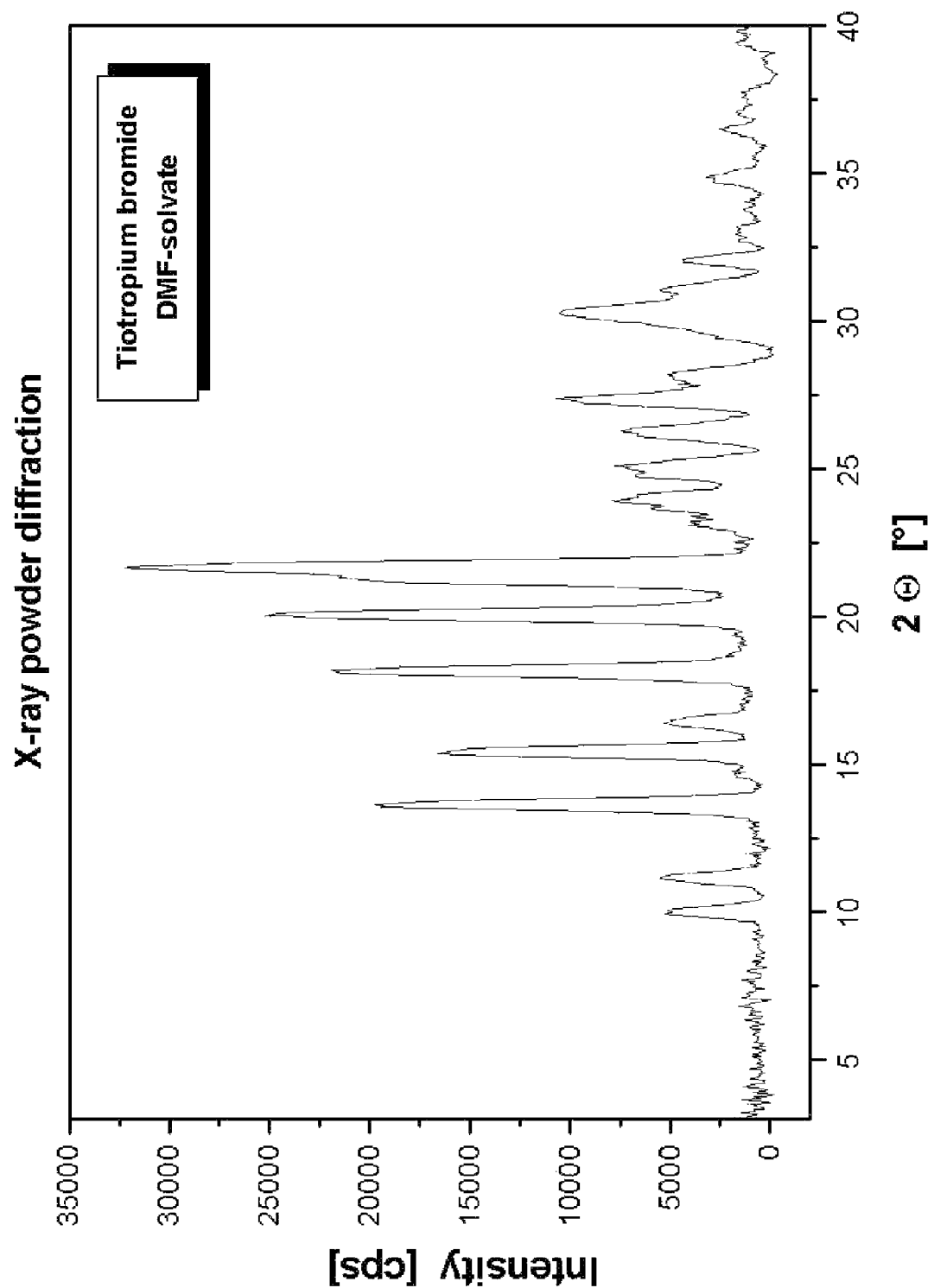
FIG. 8: X-ray powder diffraction of crystalline DMF solvate of tiotropium bromide

The X-ray powder diagram obtained for the crystalline DMF solvate of tiotropium bromide is shown in FIG. 8. The following Table 12 lists the characteristic peaks and standardised intensities.

TABLE 12

X-ray powder reflections (up to 30° 2Θ) and intensities
(normalized) of a solvated form of tiotropium bromide
containing N,N-dimethylformamide (=DMF)

| 2Θ [°] | d [Å] | I/I$_o$ [%] |
|---|---|---|
| 6.84 | 12.91 | 6 |
| 9.97 | 8.86 | 18 |
| 11.12 | 7.95 | 15 |
| 13.58 | 6.51 | 64 |
| 15.46 | 5.73 | 63 |
| 16.51 | 5.36 | 12 |
| 18.14 | 4.89 | 73 |
| 20.01 | 4.43 | 76 |
| 21.20 | 4.19 | 54 |
| 21.56 | 4.12 | 100 |
| 23.26 | 3.82 | 12 |
| 24.14 | 3.68 | 14 |
| 24.95 | 3.57 | 19 |
| 26.19 | 3.40 | 19 |
| 27.39 | 3.25 | 32 |
| 28.18 | 3.16 | 15 |
| 30.21 | 2.96 | 26 |

Characterization of Crystalline Isopropanol Solvate of Tiotropium Bromide

Figure 9:
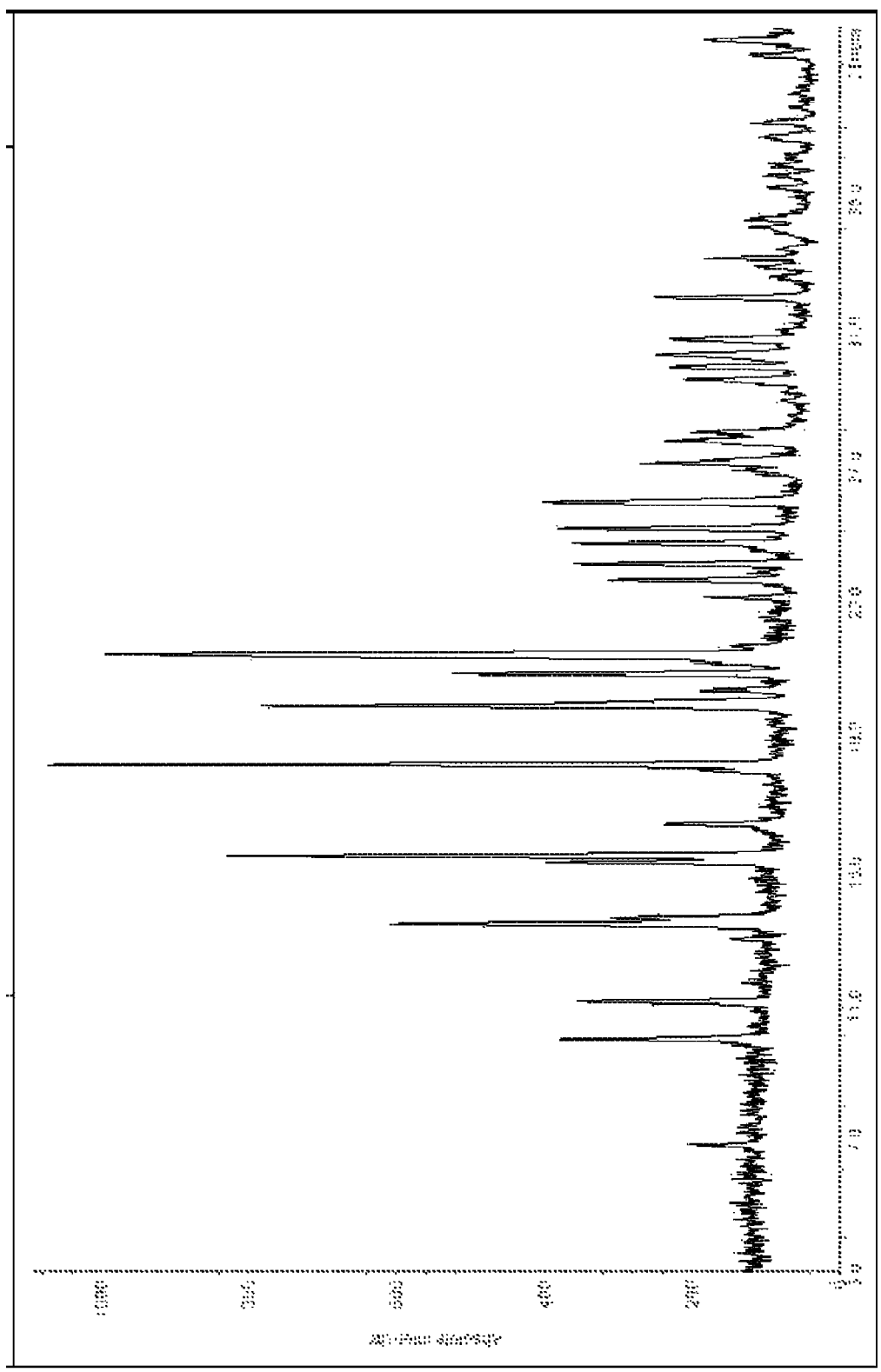
FIG. 9: X-ray powder diffraction of crystalline isopropanol solvate of tiotropium bromide

The X-ray powder diagram obtained for the crystalline isopropanol solvate of tiotropium bromide is shown in FIG. 9. The following Table 13 lists the characteristic peaks and standardised intensities.

TABLE 13

X-ray powder reflections (up to 30° 2Θ) and intensities
(normalized) of a solvated form of tiotropium bromide
containing isopropanol with a stoichiometry
of tiotropium bromide:isopropanol close to 2:1

| 2Θ [°] | d [Å] | I/I$_o$ [%] |
|---|---|---|
| 13.10 | 6.74 | 9 |
| 8.95 | 9.87 | 27 |
| 8.04 | 11.00 | 24 |
| 6.89 | 12.84 | 5 |
| 6.65 | 13.31 | 50 |
| 6.57 | 13.47 | 20 |
| 5.84 | 15.15 | 30 |
| 5.77 | 15.35 | 68 |
| 5.43 | 16.30 | 15 |
| 4.96 | 17.88 | 11 |
| 4.91 | 18.06 | 100 |
| 4.48 | 19.80 | 71 |
| 4.45 | 19.93 | 24 |
| 4.38 | 20.26 | 12 |
| 4.27 | 20.77 | 44 |
| 4.22 | 21.05 | 12 |
| 4.16 | 21.33 | 89 |
| 4.11 | 21.58 | 8 |
| 3.86 | 23.02 | 12 |
| 3.78 | 23.54 | 24 |
| 3.70 | 24.02 | 30 |
| 3.61 | 24.64 | 30 |
| 3.55 | 25.08 | 32 |
| 3.44 | 25.85 | 34 |
| 3.33 | 26.79 | 7 |
| 3.30 | 27.02 | 20 |
| 3.22 | 27.68 | 16 |
| 3.19 | 27.93 | 15 |
| 3.03 | 29.50 | 15 |
| 2.99 | 29.86 | 18 |

Characterization of Crystalline 1,2-Propanediol Solvate of Tiotropium Bromide

Figure 10:
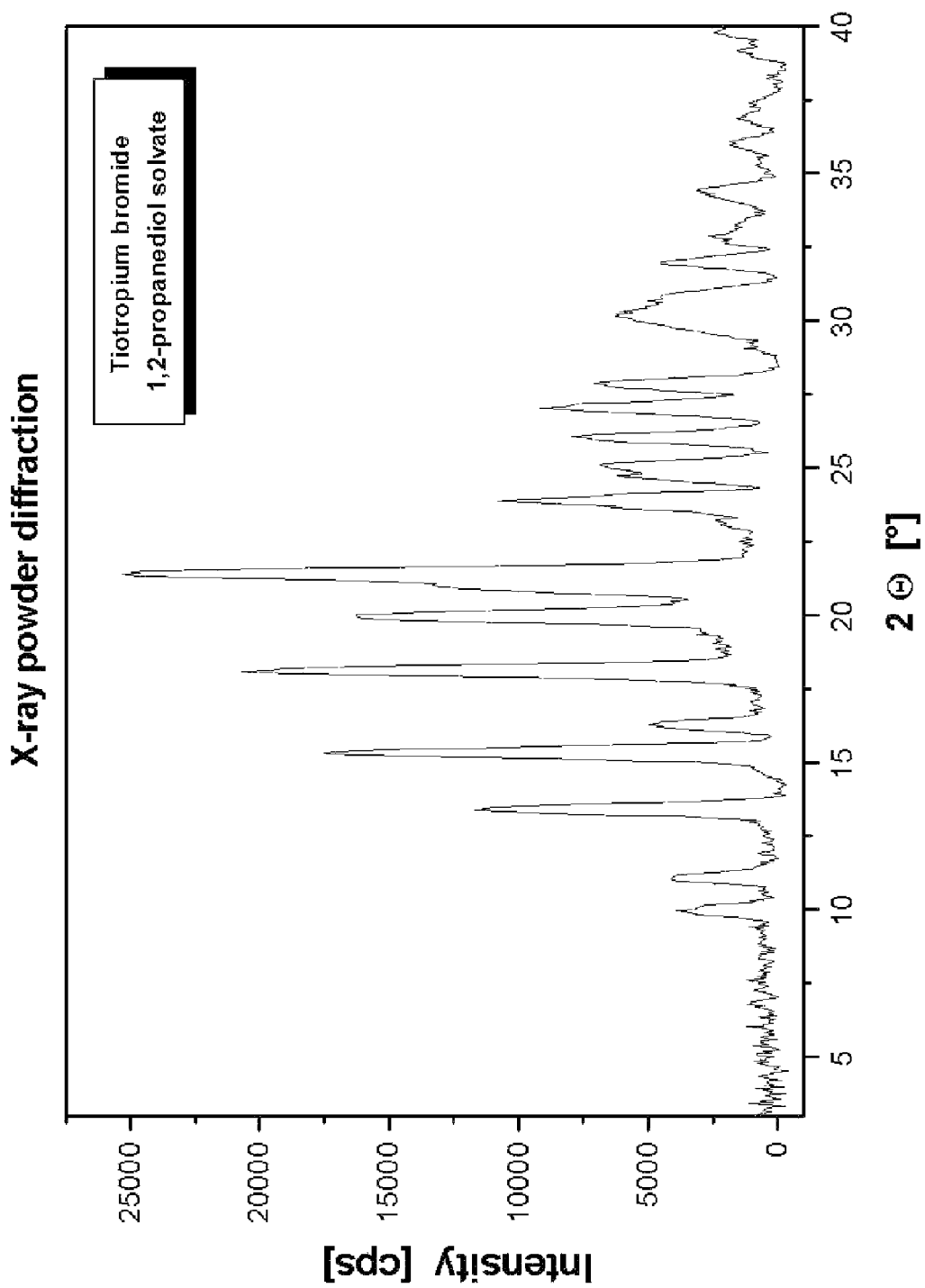
FIG. 10: X-ray powder diffraction of crystalline 1,2-propanediol solvate of tiotropium bromide

The X-ray powder diagram obtained for the crystalline 1,2-propanediol solvate of tiotropium bromide is shown in FIG. 10. The following Table 14 lists the characteristic peaks and standardised intensities.

TABLE 14

X-ray powder reflections (up to 30° 2Θ) and intensities
(normalized) of a solvated form of tiotropium bromide
containing 1,2-propanediol

| 2Θ [°] | d [Å] | I/I$_o$ [%] |
|---|---|---|
| 6.82 | 12.95 | 5 |
| 9.94 | 8.89 | 15 |
| 11.10 | 7.97 | 17 |
| 13.43 | 6.59 | 48 |
| 15.34 | 5.77 | 71 |
| 16.32 | 5.43 | 19 |
| 18.10 | 4.90 | 83 |
| 19.97 | 4.44 | 65 |
| 21.31 | 4.17 | 100 |
| 23.11 | 3.85 | 8 |
| 23.86 | 3.73 | 42 |
| 24.71 | 3.60 | 22 |
| 25.07 | 3.55 | 24 |
| 26.05 | 3.42 | 29 |
| 27.03 | 3.30 | 34 |
| 27.88 | 3.20 | 28 |
| 30.16 | 2.96 | 25 |

Characterization of Crystalline Pyridine Solvate of Tiotropium Bromide

Figure 11:
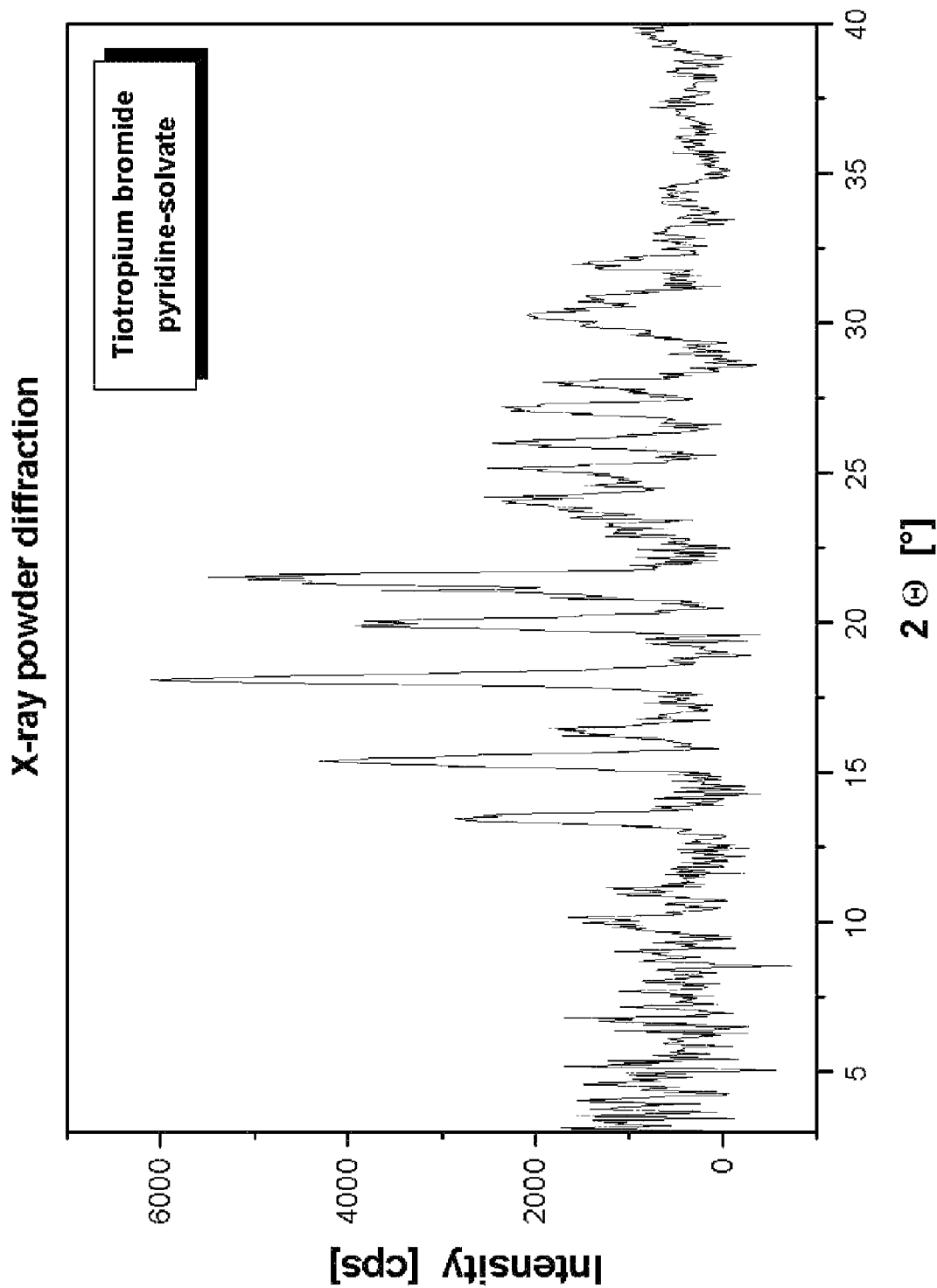
FIG. 11: X-ray powder diffraction of crystalline pyridine solvate of tiotropium bromide

The X-ray powder diagram obtained for the crystalline pyridine solvate of tiotropium bromide is shown in FIG. 11. The following Table 15 lists the characteristic peaks and standardised intensities.

TABLE 15

X-ray powder reflections (up to 30° 2Θ) and intensities (normalized) of a solvated form of tiotropium bromide containing pyridine

| 2Θ [°] | d [Å] | I/I$_o$ [%] |
|---|---|---|
| 6.76 | 13.06 | 44 |
| 9.94 | 8.89 | 24 |
| 11.22 | 7.88 | 7 |
| 13.48 | 6.57 | 46 |
| 15.38 | 5.76 | 69 |
| 16.40 | 5.40 | 24 |
| 18.13 | 4.89 | 100 |
| 19.94 | 4.45 | 62 |
| 21.36 | 4.16 | 79 |
| 23.92 | 3.72 | 30 |
| 25.08 | 3.55 | 31 |
| 25.97 | 3.43 | 31 |
| 27.11 | 3.29 | 34 |
| 27.96 | 3.19 | 30 |
| 30.27 | 2.95 | 29 |

Characterization of Crystalline tert.-butanol Solvate of Tiotropium Bromide

Figure 12:
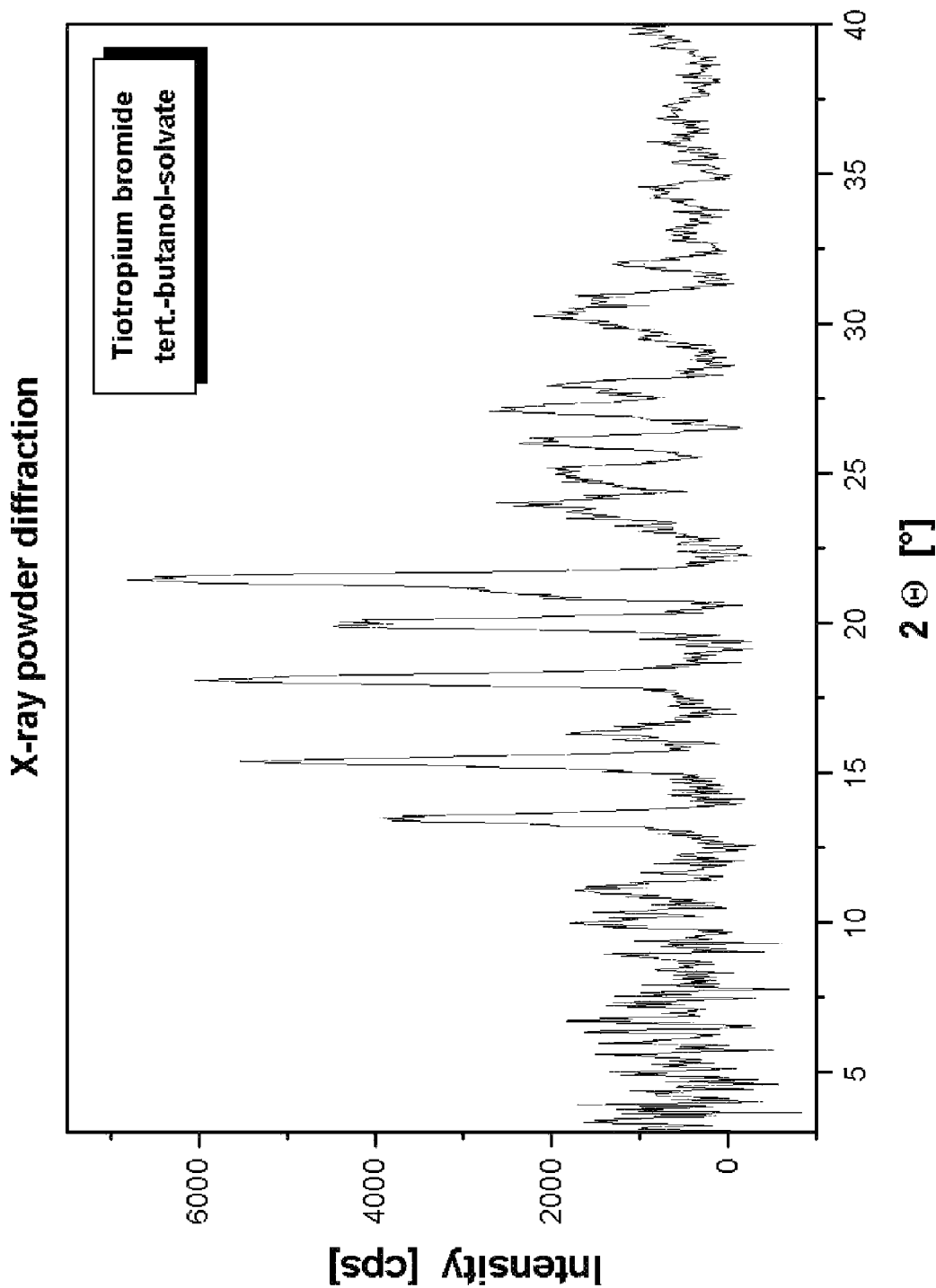
FIG. 12: X-ray powder diffraction of crystalline tert-butanol solvate of tiotropium bromide

The X-ray powder diagram obtained for the crystalline tert.-butanol solvate of tiotropium bromide is shown in FIG. 12. The following Table 16 lists the characteristic peaks and standardised intensities.

TABLE 16

X-ray powder reflections (up to 30° 2Θ) and intensities (normalized) of a solvated form of tiotropium bromide containing tert.-butanol

| 2Θ [°] | d [Å] | I/I$_o$ [%] |
|---|---|---|
| 6.73 | 13.13 | 23 |
| 10.03 | 8.81 | 21 |
| 11.08 | 7.98 | 19 |
| 13.46 | 6.57 | 58 |
| 15.38 | 5.76 | 77 |
| 16.36 | 5.41 | 17 |
| 18.13 | 4.89 | 86 |
| 19.96 | 4.44 | 64 |
| 20.97 | 4.23 | 29 |
| 21.46 | 4.14 | 100 |
| 23.86 | 3.73 | 25 |
| 24.98 | 3.56 | 19 |
| 26.04 | 3.42 | 30 |
| 27.10 | 3.29 | 36 |
| 27.95 | 3.19 | 24 |
| 30.28 | 2.95 | 22 |

Characterization of Crystalline THF Solvate of Tiotropium Bromide

Figure 13:
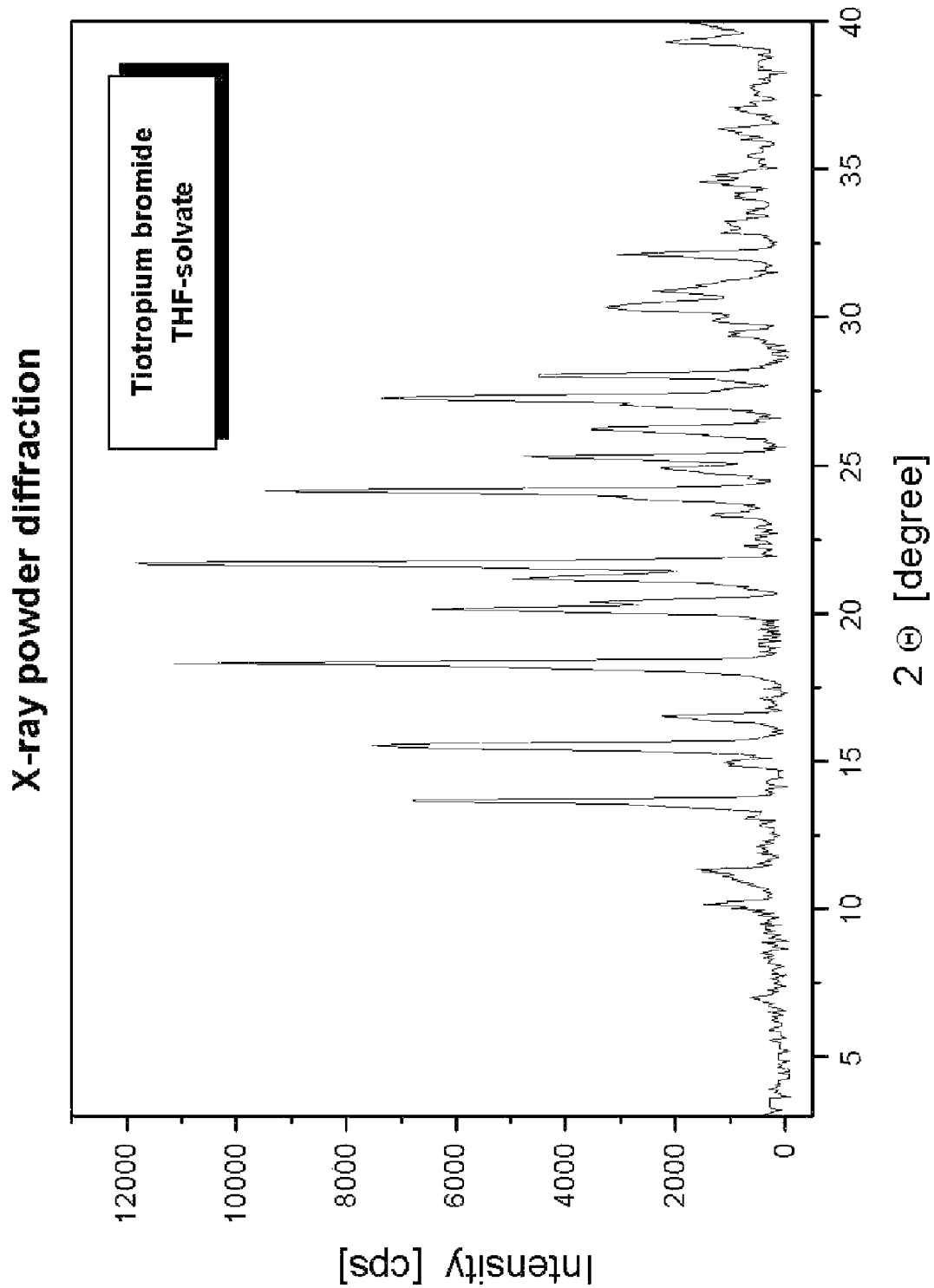
FIG. 13: X-ray powder diffraction of crystalline THF solvate of tiotropium bromide

The X-ray powder diagram obtained for the crystalline THF solvate of tiotropium bromide is shown in FIG. 13. The following Table 17 lists the characteristic peaks and standardised intensities.

TABLE 17

X-ray powder reflections (up to 30° 2Θ) and intensities (normalized) of a solvated form of tiotropium bromide containing tetrahydrofuran (=THF) with a stoichiometry of tiotropium bromide:THF close to 2:1

| 2Θ [°] | d [Å] | I/I$_o$ [%] |
|---|---|---|
| 6.98 | 12.65 | 4 |
| 10.17 | 8.69 | 10 |
| 11.28 | 7.84 | 13 |
| 13.68 | 6.47 | 58 |
| 14.95 | 5.92 | 10 |
| 15.53 | 5.70 | 65 |
| 16.48 | 5.37 | 20 |
| 18.30 | 4.85 | 95 |
| 20.11 | 4.41 | 54 |
| 20.45 | 4.34 | 29 |
| 21.19 | 4.19 | 41 |
| 21.69 | 4.09 | 100 |
| 23.31 | 3.81 | 10 |
| 24.10 | 3.69 | 79 |
| 24.89 | 3.58 | 18 |
| 25.28 | 3.52 | 39 |
| 26.20 | 3.40 | 28 |
| 27.29 | 3.27 | 60 |
| 28.02 | 3.18 | 36 |
| 29.44 | 3.03 | 7 |
| 29.92 | 2.98 | 9 |
| 30.34 | 2.94 | 26 |

Characterization of Crystalline THP Solvate of Tiotropium Bromide

Figure 14:
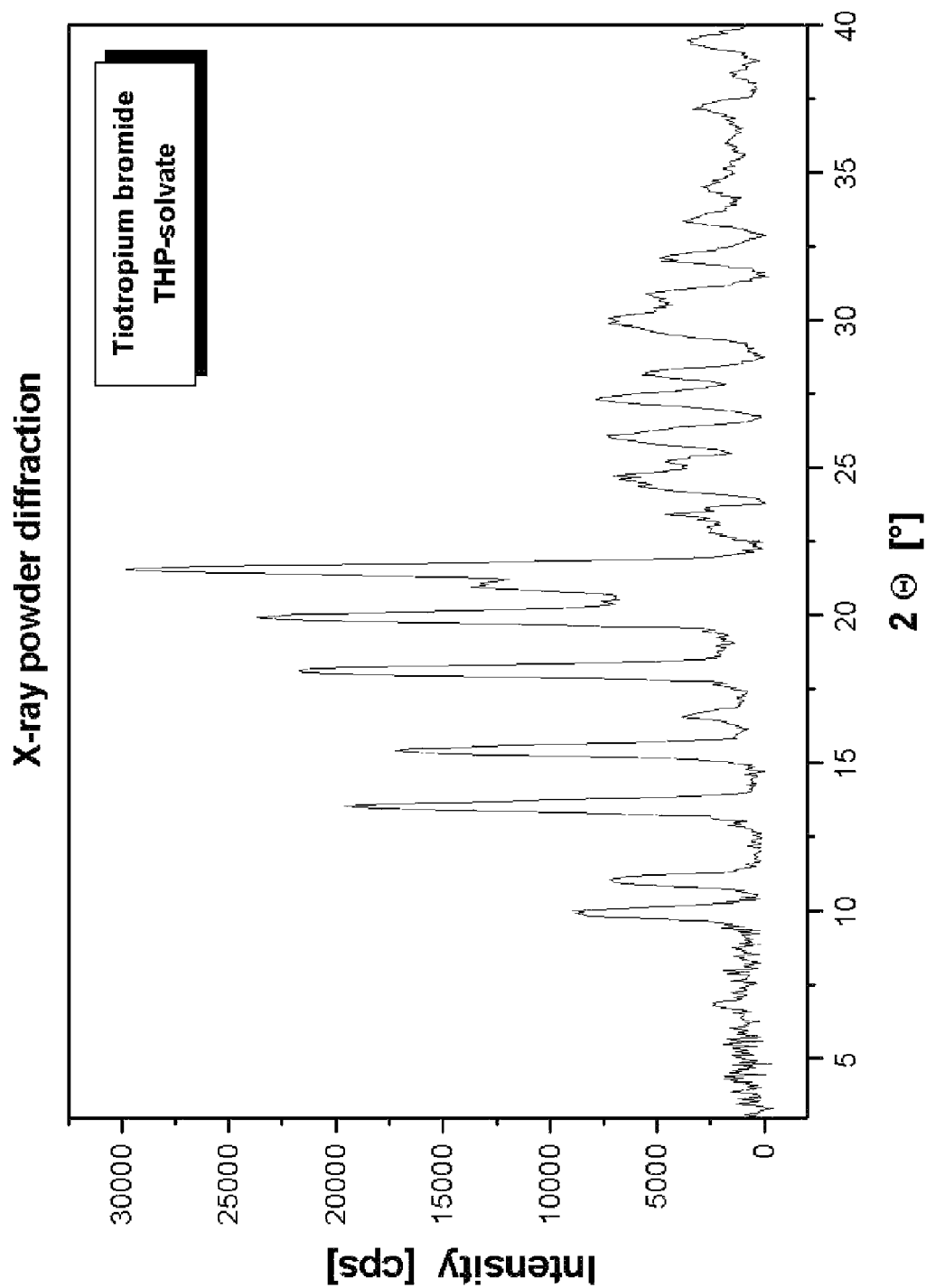
FIG. 14: X-ray powder diffraction of crystalline THP solvate of tiotropium bromide

The X-ray powder diagram obtained for the crystalline THP solvate of tiotropium bromide is shown in FIG. 14. The following Table 18 lists the characteristic peaks and standardised intensities.

TABLE 18

X-ray powder reflections (up to 30° 2Θ) and intensities (normalized) of a solvated form of tiotropium bromide containing tetrahydropyran (=THP) with a stoichiometry of tiotropium bromide:THP close to 2:1

| 2Θ [°] | d [Å] | I/I$_o$ [%] |
|---|---|---|
| 6.95 | 12.71 | 5 |
| 9.89 | 8.94 | 28 |
| 11.10 | 7.97 | 23 |
| 13.54 | 6.54 | 67 |
| 15.41 | 5.75 | 57 |
| 16.56 | 5.35 | 10 |
| 18.13 | 4.89 | 71 |
| 19.97 | 4.44 | 76 |
| 20.97 | 4.23 | 41 |
| 21.52 | 4.13 | 100 |
| 22.86 | 3.89 | 8 |
| 23.45 | 3.79 | 14 |
| 24.37 | 3.65 | 19 |
| 24.69 | 3.60 | 22 |
| 25.18 | 3.53 | 13 |
| 25.98 | 3.43 | 22 |
| 27.48 | 3.24 | 21 |
| 28.12 | 3.17 | 18 |
| 30.00 | 2.98 | 23 |

Formulations Containing the Tiotropium Bromide Forms According to the Invention

The crystalline tiotropium bromide forms according to the invention are particularly well suited to the preparation of, for example, pharmaceutical formulations for administration by inhalation such as inhalable powders or for example propellant-containing aerosol formulations, particularly inhalable powders and propellant-containing aerosol suspensions. These pharmaceutical formulations or compositions may contain in addition to the crystalline tiotropium form according to the invention one or more additional active ingredients selected from among betamimetics, EGFR inhibitors, PDEIV-inhibitors, steroids, and LTD4 antagonists, optionally together with a pharmaceutically acceptable excipient.

Inhalable Powders

The present invention also relates to inhalable powder containing 0.001 to 3% tiotropium in the form of the crystalline tiotropium bromide forms according to the invention combined with a physiologically acceptable excipient. By tiotropium is meant the ammonium cation.

Inhalable powders which contain 0.01 to 2% tiotropium are preferred according to the invention. Particularly preferred inhalable powders contain tiotropium in an amount from about 0.03 to 1%, preferably 0.05 to 0.6%, particularly preferably 0.06 to 0.3%. Of particular importance according to the invention, finally, are inhalable powders which contain about 0.08 to 0.22% tiotropium.

The amounts of tiotropium specified above are based on the amount of tiotropium cation contained.

The excipients that are used for the purposes of the present invention are prepared by suitable grinding and/or screening using current methods known in the art. The excipients used according to the invention may also be mixtures of excipients which are obtained by mixing excipient fractions of different mean particle sizes.

Examples of physiologically acceptable excipients which may be used to prepare the inhalable powders for use in the inhalettes according to the invention include monosaccharides (e.g. glucose, fructose or arabinose), disaccharides (e.g. lactose, saccharose, maltose, trehalose), oligo- and polysaccharides (e.g. dextrans, dextrins, maltodextrin, starch, cellulose), polyalcohols (e.g. sorbitol, mannitol, xylitol), cyclodextrins (e.g. α-cyclodextrin, β-cyclodextrin, χ-cyclodextrin, methyl-β-cyclodextrin, hydroxypropyl-β-cyclodextrin), amino acids (e.g. arginine hydrochloride) or salts (e.g. sodium chloride, calcium carbonate), or mixtures thereof. Preferably, mono- or disaccharides are used, while the use of lactose or glucose is preferred, particularly, but not exclusively, in the form of their hydrates. For the purposes of the invention, lactose is the particularly preferred excipient.

Within the scope of the inhalable powders according to the invention the excipients have a maximum average particle size of up to 250 μm, preferably between 10 and 150 μm, most preferably between 15 and 80 μm. It may sometimes seem appropriate to add finer excipient fractions with an average particle size of 1 to 9 μm to the excipients mentioned above. These finer excipients are also selected from the group of possible excipients listed hereinbefore. The average particle size may be determined using methods known in the art (cf. for example WO 02/30389, paragraphs A and C). Finally, in order to prepare the inhalable powders according to the invention, micronised crystalline tiotropium bromide anhydrate, which is preferably characterised by an average particle size of 0.5 to 10 μm, particularly preferably from 1 to 5 μm, is added to the excipient mixture (cf. for example WO 02/30389, paragraph B). Processes for grinding and micronising active substances are known from the prior art.

If no specifically prepared excipient mixture is used as the excipient, it is particularly preferable to use excipients which have a mean particle size of 10-50 μm and a 10% fine content of 0.5 to 6 μm.

By average particle size is meant here the 50% value of the volume distribution measured with a laser diffractometer using the dry dispersion method. The average particle size may be determined using methods known in the art (cf. for example WO 02/30389, paragraphs A and C). Analogously, the 10% fine content in this instance refers to the 10% value of the volume distribution measured using a laser diffractometer. In other words, for the purposes of the present invention, the 10% fine content denotes the particle size below which 10% of the quantity of particles is found (based on the volume distribution).

The percentages given within the scope of the present invention are always percent by weight, unless specifically stated to the contrary.

In particularly preferred inhalable powders the excipient is characterised by a mean particle size of 12 to 35 μm, particularly preferably from 13 to 30 μm.

Also particularly preferred are those inhalable powders wherein the 10% fine content is about 1 to 4 μm, preferably about 1.5 to 3 μm.

The inhalable powders according to the invention are characterised, in accordance with the problem on which the invention is based, by a high degree of homogeneity in the sense of the accuracy of single doses. This is in the region of <8%, preferably <6%, most preferably <4%.

After the starting materials have been weighed out the inhalable powders are prepared from the excipient and the active substance using methods known in the art. Reference may be made to the disclosure of WO 02/30390, for example. The inhalable powders according to the invention may accordingly be obtained by the method described below, for example. In the preparation methods described hereinafter the components are used in the proportions by weight described in the above-mentioned compositions of the inhalable powders.

First, the excipient and the active substance are placed in a suitable mixing container. The active substance used has an average particle size of 0.5 to 10 μm, preferably 1 to 6 μm, most preferably 2 to 5 μm. The excipient and the active substance are preferably added using a sieve or a granulating sieve with a mesh size of 0.1 to 2 mm, preferably 0.3 to 1 mm, most preferably 0.3 to 0.6 mm. Preferably, the excipient is put in first and then the active substance is added to the mixing container. During this mixing process the two components are preferably added in batches. It is particularly preferred to sieve in the two components in alternate layers. The mixing of the excipient with the active substance may take place while the two components are still being added. Preferably, however, mixing is only done once the two components have been sieved in layer by layer.

The present invention also relates to the use of the inhalable powders according to the invention for preparing a pharmaceutical composition for the treatment of respiratory complaints, particularly for the treatment of COPD and/or asthma.

The inhalable powders according to the invention may for example be administered using inhalers which meter a single dose from a reservoir by means of a measuring chamber (e.g. according to U.S. Pat. No. 4,570,630A) or by other means (e.g. according to DE 36 25 685 A). Preferably, however, the inhalable powders according to the invention are packed into capsules (to make so-called inhalettes), which are used in inhalers such as those described in WO 94/28958, for example.

Figure 15:
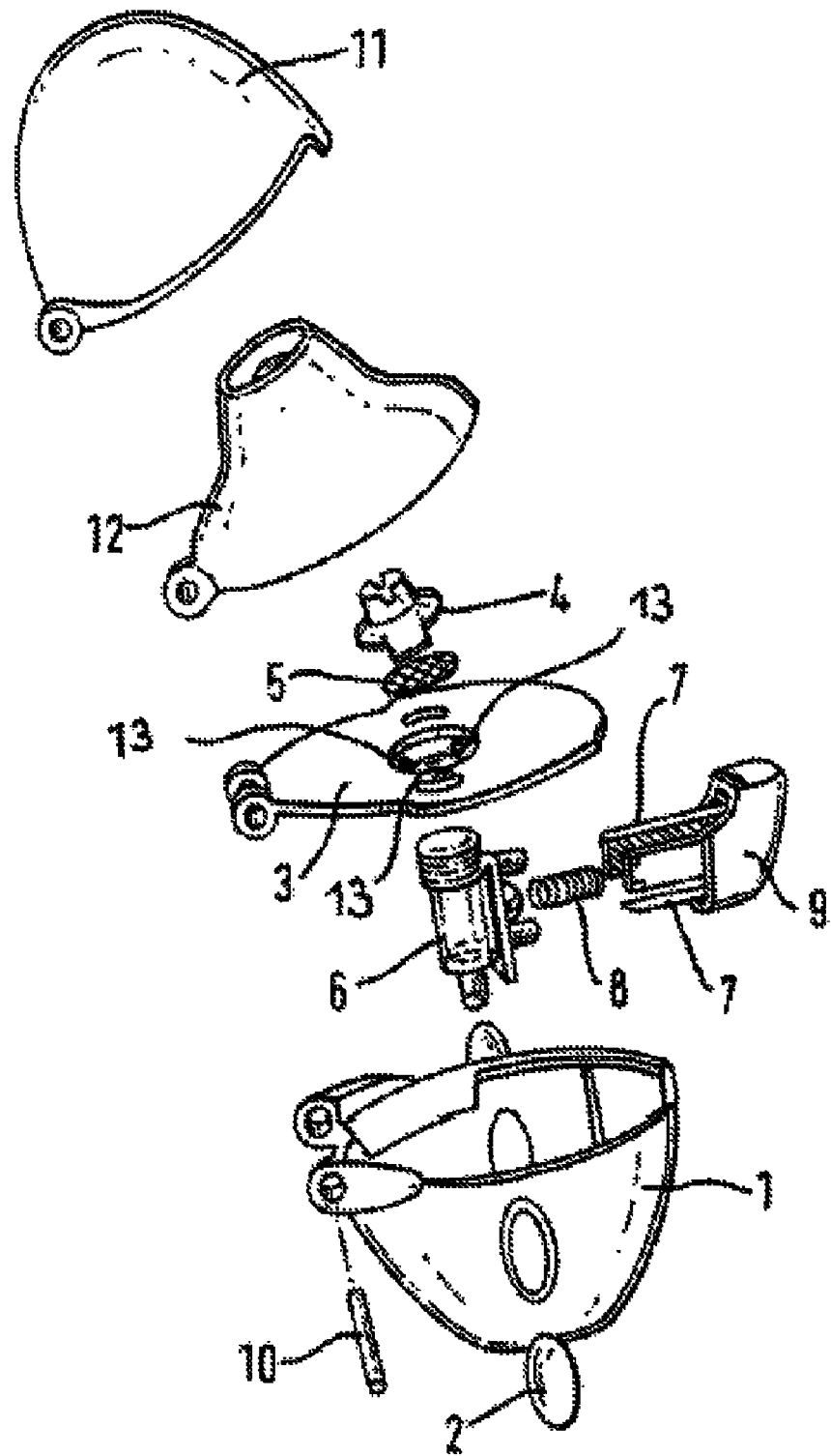
FIG. 15: Exploded view of a preferred inhaler for administration of the pharmaceutical compositions described herein

Most preferably, the capsules containing the inhalable powder according to the invention are administered using an inhaler as shown in FIG. 15. This inhaler is characterised by a housing 1 containing two windows 2, a deck 3 in which there are air inlet ports and which is provided with a screen 5 secured via a screen housing 4, an inhalation chamber 6 connected to the deck 3 on which there is a push button 9 provided with two sharpened pins 7 and movable counter to a spring 8, and a mouthpiece 12 which is connected to the housing 1, the deck 3 and a cover 11 via a spindle 10 to enable it to be flipped open or shut and airholes 13 for adjusting the flow resistance.

The present invention further relates to the use of the inhalable powders containing one or several, preferably one of the crystalline tiotropium bromide forms according to the invention for preparing a pharmaceutical composition for treating respiratory complaints, particularly for the treatment of COPD and/or asthma, characterised in that the inhaler described above and shown in FIG. 15 is used.

For administering the inhalable powders containing the crystalline tiotropium bromide forms according to the invention using powder-filled capsules it is particularly preferred to use capsules the material of which is selected from among the synthetic plastics, most preferably selected from among polyethylene, polycarbonate, polyester, polypropylene and polyethylene terephthalate. Particularly preferred synthetic plastic materials are polyethylene, polycarbonate or polyethylene terephthalate. If polyethylene is used as one of the capsule materials which is particularly preferred according to the invention, it is preferable to use polyethylene with a density of between 900 and 1000 kg/m$^3$, preferably 940-980 kg/m$^3$, more preferably about 960-970 kg/m$^3$ (high density polyethylene). The synthetic plastics according to the invention may be processed in various ways using manufacturing methods known in the art. Injection moulding of the plastics is preferred according to the invention. Injection moulding without the use of mould release agents is particularly preferred. This method of production is well defined and is characterised by being particularly reproducible.

In another aspect the present invention relates to the abovementioned capsules which contain the abovementioned inhalable powder according to the invention. These capsules may contain about 1 to 20 mg, preferably about 3 to 15 mg, most preferably about 4 to 12 mg of inhalable powder. Preferred formulations according to the invention contain 4 to 6 mg of inhalable powder. Of equivalent importance according to the invention are capsules for inhalation which contain the formulations according to the invention in an amount of from 8 to 12 mg.

The present invention also relates to an inhalation kit consisting of one or more of the above capsules characterised by a content of inhalable powder according to the invention in conjunction with the inhaler according to FIG. 15.

The present invention also relates to the use of the abovementioned capsules characterised by a content of inhalable powder according to the invention, for preparing a pharmaceutical composition for treating respiratory complaints, especially for treating COPD and/or asthma.

Filled capsules which contain the inhalable powders according to the invention are produced by methods known in the art, by filling the empty capsules with the inhalable powders according to the invention.

Examples of Inhalable Powders According to the Invention

The following Examples serve to illustrate the present invention in more detail without restricting the scope of the invention to the exemplifying embodiments that follow.

Active Substance

The crystalline tiotropium bromide forms according to the invention are used to produce the inhalable powders according to the invention. The micronisation of these forms may be carried out analogously to methods known in the art (cf for example WO 03/078429 A1). Where reference is made within the scope of the present invention to the mean particle size of the crystalline tiotropium bromide forms according to the invention, this is determined using methods of measurement known in the art (cf for example WO 03/078429 A1, para. D.2).

Excipient:

In the Examples that follow lactose-monohydrate is used as excipient. It may be obtained for example from Borculo Domo Ingredients, Borculo/NL under the product name Lactochem Extra Fine Powder. The specifications according to the invention for the particle size and specific surface area are met by this grade of lactose. For example, in the Examples that follow, batches of lactose were used having the following specifications:

Preparation of the Powder Formulations:

Apparatus

The following machines and equipment, for example, may be used to prepare the inhalable powders:

Mixing container or powder mixer: Turbulamischer 2 L, Type 2C; made by Willy A. Bachofen AG, CH-4500 Basel Hand-Held screen: 0.135 mm mesh size The empty inhalation capsules may be filled with inhalable powders containing tiotropium by hand or mechanically. The following equipment may be used.

Capsule Filling Machine:

MG2, Type G100, manufacturer: MG2 S.r.1, I-40065 Pian di Macina di Pianoro (BO), Italy Formulation Examples Formulation Example 1

Powder Mixture

To prepare the powder mixture, 299.39 g of excipient and 0.61 g of micronised crystalline tiotropium bromide anhydrate are used.

About 40-45 g of excipient are placed in a suitable mixing container through a hand-held screen with a mesh size of 0.315 mm. Then crystalline tiotropium bromide anhydrate in batches of about 90-110 mg and excipient in batches of about 40-45 g are screened in in alternate layers. The excipient and active substance are added in 7 and 6 layers, respectively.

Having been screened in, the ingredients are then mixed (mixing speed 900 rpm). The final mixture is passed twice more through a hand-held screen and then mixed again at 900 rpm.

Using the method described in formulation Example 1 it is possible to obtain inhalable powders which when packed into suitable plastic capsules may be used to produce the following capsules for inhalation, for example:

Formulation Example 2

| | |
|---|---|
| tiotropium bromide anhydrate: | 0.0113 mg |
| lactose monohydrate: | 5.4887 mg |
| capsule: | 100.0 mg |
| Total: | 105.5 mg |

Formulation Example 3

| | |
|---|---|
| tiotropium bromide anhydrate: | 0.0225 mg |
| lactose monohydrate: | 5.4775 mg |
| polyethylene capsules: | 100.0 mg |
| Total: | 105.5 mg |

Formulation Example 4

| | |
|---|---|
| tiotropium bromide anhydrate: | 0.0056 mg |
| lactose monohydrate: | 5.4944 mg |
| polyethylene capsules: | 100.0 mg |
| Total: | 105.5 mg |

Formulation Example 5

| | |
|---|---|
| tiotropium bromide anhydrate: | 0.0113 mg |
| lactose monohydrate:* | 5.4887 mg |
| capsule: | 100.0 mg |
| Total: | 105.5 mg |

*the lactose contains 5% specifically added fine content of micronised lactose monohydrate with a mean particle size of about 4 µm.

Formulation Example 6

| | |
|---|---|
| tiotropium bromide anhydrate: | 0.0225 mg |
| lactose monohydrate:* | 5.4775 mg |
| polyethylene capsules: | 100.0 mg |
| Total: | 105.5 mg |

*the lactose contains 5% specifically added fine content of micronised lactose monohydrate with a mean particle size of about 4 µm.

Formulation Example 7

| | |
|---|---|
| tiotropium bromide anhydrate: | 0.0056 mg |
| lactose monohydrate:* | 5.4944 mg |
| polyethylene capsules: | 100.0 mg |
| Total: | 105.5 mg |

*the lactose contains 5% specifically added fine content of micronised lactose monohydrate with a mean particle size of about 4 µm.

It is apparent for the person of ordinary skill in the art, that the foregoing examples can be applied in analogy with one of the other crystalline forms of tiotropium bromide specified hereinbefore. In order to obtain products comprising one of the other solvates according to the invention the powder mixture according to formulation example 1 and also formulation examples 2 to 7 can easily be obtained by using one of the other crystalline solvates according to the invention instead of the tiotropium bromide anhydrate.

Propellant-Containing Aerosol Suspensions

The crystalline tiotropium bromide forms according to the invention may optionally also be administered in the form of propellant-containing inhalable aerosols. Aerosol suspensions are particularly suitable for this.

The present invention therefore also relates to suspensions of the crystalline tiotropium bromide forms according to the invention in the propellent gases HFA 227 and/or HFA 134a, optionally combined with one or more other propellent gases, preferably selected from the group consisting of propane, butane, pentane, dimethylether, $CHClF_2$, $CH_2F_2$, $CF_3CH_3$, isobutane, isopentane and neopentane.

According to the invention those suspensions which contain as propellent gas only HFA 227, a mixture of HFA 227 and HFA 134a or only HFA 134a are preferred.

If a mixture of the propellent gases HFA 227 and HFA 134a is used in the suspension formulations according to the invention, the weight ratios in which these two propellent gas components are used are freely variable.

If one or more other propellent gases, selected from the group consisting of propane, butane, pentane, dimethylether, $CHClF_2$, $CH_2F_2$, $CF_3CH_3$, isobutane, isopentane and neopentane are used in addition to the propellent gases HFA 227 and/or HFA 134a in the suspension formulations according to the invention, the amount of this additional propellent gas component is preferably less than 50%, preferably less than 40%, particularly preferably less than 30%.

The suspensions according to the invention preferably contain an amount of tiotropium bromide form such that the amount of tiotropium cation is between 0.001 and 0.8%, preferably between 0.08 and 0.5%, and particularly preferably between 0.2 and 0.4% according to the invention.

Unless stated to the contrary, the percentages given within the scope of the present invention are always percent by weight.

In some cases, the term suspension formulation is used within the scope of the present invention instead of the term suspension. The two terms are to be regarded as equivalent within the scope of the present invention.

The propellant-containing inhalable aerosols or suspension formulations according to the invention may also contain other constituents such as surface-active agents (surfactants), adjuvants, antioxidants or flavourings.

The surface-active agents (surfactants) optionally present in the suspensions according to the invention are preferably selected from the group consisting of Polysorbate 20, Polysorbate 80, Myvacet 9-45, Myvacet 9-08, isopropyl myristate, oleic acid, propyleneglycol, polyethyleneglycol, Brij, ethyl oleate, glyceryl trioleate, glyceryl monolaurate, glyceryl monooleate, glyceryl monostearate, glyceryl monoricinoleate, cetylalcohol, sterylalcohol, cetylpyridinium chloride, block polymers, natural oil, ethanol and isopropanol. Of the above-mentioned suspension adjuvants Polysorbate 20, Polysorbate 80, Myvacet 9-45, Myvacet 9-08 or isopropyl myristate are preferably used. Myvacet 9-45 or isopropyl myristate are most preferably used.

If the suspensions according to the invention contain surfactants these are preferably used in an amount of 0.0005-1%, particularly preferably 0.005-0.5%.

The adjuvants optionally contained in the suspensions according to the invention are preferably selected from the group consisting of alanine, albumin, ascorbic acid, aspartame, betaine, cysteine, phosphoric acid, nitric acid, hydrochloric acid, sulphuric acid and citric acid. Ascorbic acid, phosphoric acid, hydrochloric and citric acid are preferable used, while hydrochloric acid or citric acid is most preferably used.

If adjuvants are present in the suspensions according to the invention, these are preferably used in an amount of 0.0001-1.0%, preferably 0.0005-0.1%, particularly preferably 0.001-0.01%, while an amount of 0.001-0.005% is particularly important according to the invention.

The antioxidants optionally contained in the suspensions according to the invention are preferably selected from the group consisting of ascorbic acid, citric acid, sodium edetate, editic acid, tocopherols, butylhydroxytoluene, butylhydroxyanisol and ascorbylpalmitate, while tocopherols, butylhydroxytoluene, butylhydroxyanisol or ascorbylpalmitate are preferably used.

The flavourings optionally contained in the suspensions according to the invention are preferably selected from the group consisting of peppermint, saccharine, Dentomint, aspartame and ethereal oils (for example cinnamon, aniseed, menthol, camphor), of which peppermint or Dentomint® are particularly preferred.

With a view to administration by inhalation it is essential to provide the active substances in finely divided form. For this purpose, the crystalline tiotropium bromide forms according to the invention are obtained in finely divided form using methods known in the prior art. Methods of micronising active substances are known in the art. Preferably after micronising the active substance has a mean particle size of 0.5 to 10 µm, preferably 1 to 6 µm, particularly preferably 1.5 to 5 µm. Preferably at least 50%, preferably at least 60%, particularly preferably at least 70% of the particles of active substance have a particle size which is within the size ranges mentioned above. Particularly preferably at least 80%, most preferably at least 90% of the particles of active substance have a particle size which is within the size ranges mentioned above.

In another aspect the present invention relates to suspensions which contain only one of the two active substances according to the invention without any other additives.

The suspensions according to the invention may be prepared using methods known in the art. For this, the constituents of the formulation are mixed with the propellant gas or gases (optionally at low temperatures) and filled into suitable containers.

The above-mentioned propellant-containing suspensions according to the invention may be administered using inhalers known in the art (pMDIs=pressurized metered dose inhalers). Accordingly, in another aspect, the present invention relates to pharmaceutical compositions in the form of suspensions as hereinbefore described combined with one or more inhalers suitable for administering these suspensions. Moreover the present invention relates to inhalers, characterised in that they contain the propellant-containing suspensions according to the invention described hereinbefore.

The present invention also relates to containers (cartridges) which when fitted with a suitable valve can be used in a suitable inhaler and which contain one of the above-mentioned propellant-containing suspensions according to the invention. Suitable containers (cartridges) and processes for filling these cartridges with the propellant-containing suspensions according to the invention are known in the art.

In view of the pharmaceutical activity of tiotropium the present invention also relates to the use of the suspensions according to the invention for preparing a pharmaceutical composition for inhalation or nasal administration, preferably for preparing a pharmaceutical composition for inhalative or nasal treatment of diseases in which anticholinergics may develop a therapeutic benefit.

Particularly preferably the present invention also relates to the use of the suspensions according to the invention for preparing a pharmaceutical composition for the inhalative treatment of respiratory complaints, preferably asthma or COPD.

The Examples that follow serve to illustrate the present invention in more detail, by way of example, without restricting it to their contents.

Examples of Aerosol Suspension Formulations

Suspensions containing other ingredients in addition to active substance and propellant gas:

Formulation Example 8

| constituents | concentration [% w/w] |
|---|---|
| tiotropium bromide anhydrate | 0.04 |
| oleic acid | 0.005 |
| HFA-227 | 99.955 |

Formulation Example 9

| constituents | concentration [% w/w] |
|---|---|
| tiotropium bromide anhydrate | 0.02 |
| oleic acid | 0.01 |
| HFA-227 | 60.00 |
| HFA-134a | 39.97 |

Formulation Example 10

| constituents | concentration [% w/w] |
|---|---|
| tiotropium bromide anhydrate | 0.02 |
| isopropylmyristate | 1.00 |
| HFA-227 | 98.98 |

Formulation Example 11

| constituents | concentration [% w/w] |
|---|---|
| tiotropium bromide anhydrate | 0.02 |
| Myvacet 9-45 | 0.3 |
| HFA-227 | 99.68 |

Formulation Example 12

| constituents | concentration [% w/w] |
|---|---|
| tiotropium bromide anhydrate | 0.02 |
| Myvacet 9-45 | 0.1 |
| HFA-227 | 60.00 |
| HFA-134a | 39.88 |

Formulation Example 13

| constituents | concentration [% w/w] |
|---|---|
| tiotropium bromide anhydrate | 0.04 |
| Polysorbate 80 | 0.04 |
| HFA-227 | 99.92 |

Formulation Example 14

| constituents | concentration [% w/w] |
|---|---|
| tiotropium bromide anhydrate | 0.01 |
| Polysorbate 20 | 0.20 |
| HFA-227 | 99.78 |

Formulation Example 15

| constituents | concentration [% w/w] |
|---|---|
| tiotropium bromide anhydrate | 0.04 |
| Myvacet 9-08 | 01.00 |
| HFA-227 | 98.96 |

Formulation Example 16

| constituents | concentration [% w/w] |
|---|---|
| tiotropium bromide anhydrate | 0.02 |
| isopropylmyristate | 0.30 |
| HFA-227 | 20.00 |
| HFA-134a | 79.68 |

Formulation Example 17

| constituents | concentration [% w/w] |
|---|---|
| tiotropium bromide anhydrate | 0.02 |
| HFA-227 | 60.00 |
| HFA-134a | 39.98 |

Formulation Example 18

| constituents | concentration [% w/w] |
|---|---|
| tiotropium bromide anhydrate | 0.02 |
| HFA-227 | 99.98 |

Formulation Example 19

| constituents | concentration [% w/w] |
|---|---|
| tiotropium bromide anhydrate | 0.02 |
| HFA-134a | 99.98 |

Formulation Example 20

| constituents | concentration [% w/w] |
|---|---|
| tiotropium bromide anhydrate | 0.02 |
| HFA-227 | 99.98 |

Formulation Example 21

| constituents | concentration [% w/w] |
|---|---|
| tiotropium bromide anhydrate | 0.02 |
| HFA-134a | 99.98 |

Formulation Example 22

| constituents | concentration [% w/w] |
|---|---|
| tiotropium bromide anhydrate | 0.02 |
| HFA-227 | 20.00 |
| HFA-134a | 79.98 |

Formulation Example 23

| constituents | concentration [% w/w] |
|---|---|
| tiotropium bromide anhydrate | 0.04 |
| HFA-227 | 40.00 |
| HFA-134a | 59.96 |

Formulation Example 24

| constituents | concentration [% w/w] |
|---|---|
| tiotropium bromide anhydrate | 0.04 |
| HFA-227 | 80.00 |
| HFA-134a | 19.96 |

It is apparent for the person of ordinary skill in the art, that the foregoing examples can be applied in analogy with one of the other crystalline forms of tiotropium bromide specified hereinbefore. In order to obtain products comprising one of the other solvates according to the invention the formulation examples 8 to 24 can easily be obtained by using one of the other crystalline solvates according to the invention instead of the tiotropium bromide anhydrate.

We claim:

1. A crystalline anisol solvate of tiotropium bromide characterized by an X-ray powder diffraction pattern with a characteristic value d=4.14 Å.

2. The crystalline anisol solvate of tiotropium bromide according to claim 1, further characterized by an X-ray powder diffraction pattern with characteristic values d=4.88 Å and 4.14 Å.

3. The crystalline anisol solvate of tiotropium bromide according to claim 2, further characterized by an X-ray powder diffraction with characteristic values d=6.55 Å, 4.88 Å and 4.14 Å.

4. A crystalline n-butanol solvate of tiotropium bromide characterized by an X-ray powder diffraction pattern with a characteristic value d=21.41 Å.

5. The crystalline n-butanol solvate of tiotropium bromide according to claim 4, further characterized by a X-ray powder diffraction pattern with characteristic values d=17.95 Å and 21.41 Å.

6. The crystalline n-butanol solvate of tiotropium bromide according to claim 5, further characterized by an X-ray powder diffraction pattern with characteristic values d=13.38 Å, 17.95 Å and 21.41 Å.

7. A crystalline N,N-dimethylacetamide solvate of tiotropium bromide characterized by an X-ray powder diffraction pattern with a characteristic value d=4.10 Å.

8. The crystalline N,N-dimethylacetamide solvate of tiotropium bromide according to claim 7, further characterized by an X-ray powder diffraction pattern with characteristic values d=4.42 Å and 4.10 Å.

9. The crystalline N,N-dimethylacetamide solvate of tiotropium bromide according to claim 8, further characterized by an X-ray powder diffraction pattern with characteristic values d=4.89 Å, 4.42 Å and 4.10 Å.

10. A crystalline N,N-dimethylformamide solvate of tiotropium bromide characterized by an X-ray powder diffraction pattern with a characteristic value d=4.12 Å.

11. The crystalline N,N-dimethylformamide solvate of tiotropium bromide according to claim 10, further characterized by an X-ray powder diffraction pattern with characteristic values d=4.43 Å and 4.12 Å.

12. The crystalline N,N-dimethylformamide solvate of tiotropium bromide according to claim 11, further characterized by an X-ray powder diffraction pattern with characteristic values d=4.89 Å, 4.43 Å and 4.12 Å.

13. A crystalline isopropanol solvate of tiotropium bromide according to claim 1, further characterized by an X-ray powder diffraction pattern with a characteristic value d=18.06 Å.

14. The crystalline isopropanol solvate of tiotropium bromide according to claim 13, further characterized by an X-ray powder diffraction pattern with characteristic values d=18.06 Å and 21.33 Å.

15. The crystalline isopropanol solvate of tiotropium bromide according to claim 14, further characterized by an X-ray powder diffraction pattern with characteristic values d=18.06 Å, 19.80 Å and 21.33 Å.

16. A crystalline 1,2-propanediol solvate of tiotropium bromide characterized by an X-ray powder diffraction pattern with a characteristic value d=4.17 Å.

17. The crystalline 1,2-propanediol solvate of tiotropium bromide according to claim 16, further characterized by an X-ray powder diffraction pattern with characteristic values d=4.90 Å and 4.17 Å.

18. The crystalline 1,2-propanediol solvate of tiotropium bromide according to claim 17, further characterized by an X-ray powder diffraction pattern with characteristic values d=4.90 Å, 4.44 Å and 4.17 Å.

19. A crystalline pyridine solvate of tiotropium bromide characterized by an X-ray powder diffraction pattern with a characteristic value d=4.89 Å.

20. The crystalline pyridine solvate of tiotropium bromide according to claim 19, further characterized by an X-ray powder diffraction pattern with characteristic values d=4.89 Å and 4.16 Å.

21. The crystalline pyridine solvate of tiotropium bromide according to claim 20, further characterized by an X-ray powder diffraction pattern with characteristic values d=5.76 Å, 4.89 Å and 4.16 Å.

22. A crystalline tert-butanol solvate of tiotropium bromide characterized by an X-ray powder diffraction pattern with a characteristic value d=4.14 Å.

23. The crystalline tert-butanol solvate of tiotropium bromide according to claim 22, characterized by an X-ray powder diffraction pattern with characteristic values d=4.89 Å and 4.14 Å.

24. The crystalline tert-butanol solvate of tiotropium bromide according to claim 23, further characterized by an X-ray powder diffraction pattern with characteristic values d=5.76 Å, 4.89 Å and 4.14 Å.

25. A crystalline tetrahydrofuran solvate of tiotropium bromide characterized by an X-ray powder diffraction pattern with a characteristic value d=4.09 Å.

26. The crystalline tetrahydrofuran solvate of tiotropium bromide according to claim 25, further characterized by an X-ray powder diffraction pattern with characteristic values d=4.85 Å and 4.09 Å.

27. The crystalline tetrahydrofuran solvate of tiotropium bromide according to claim 26, further characterized by an X-ray powder diffraction pattern with characteristic values d=4.85 Å, 4.09 Å and 3.69 Å.

28. A crystalline tetrahydropyran solvate of tiotropium bromide characterized by an X-ray powder diffraction pattern with a characteristic value d=4.13 Å.

29. The crystalline tetrahydropyran solvate of tiotropium bromide according to claim 28, further characterized by an X-ray powder diffraction pattern with characteristic values d=4.44 Å and 4.13 Å.

30. The crystalline tetrahydropyran solvate of tiotropium bromide according to claim 29, further characterized by an X-ray powder diffraction pattern with characteristic values d=4.89 Å, 4.44 Å and 4.13 Å.

31. A method of preparing the crystalline isopropanol solvate of tiotropium bromide of claim 13, comprising drying crystalline tiotropium bromide monohydrate at a temperature of 60-90° C., dissolving the crystalline tiotropium bromide monohydrate in a methanol-containing solvent to form a solution, adding the solution to an isopropanol-containing solvent, cooling to a temperature below 15° C., isolating and drying the crystals.

32. A method of preparing the crystalline n-butanol solvate of tiotropium bromide of claim 4, comprising drying crystalline tiotropium bromide monohydrate at a temperature of 60-90° C., dissolving the crystalline tiotropium bromide monohydrate in a methanol-containing solvent to form a solution, adding the solution to a n-butanol-containing solvent, cooling to a temperature below 15° C., isolating and drying the crystals.

33. A method of preparing the crystalline tetrahydrofuran solvate of tiotropium bromide of claim 25, comprising drying crystalline tiotropium bromide monohydrate at a temperature of 60-90° C., dissolving the crystalline tiotropium bromide monohydrate in a methanol-containing solvent to form a solution, adding the solution to a tetrahyrofuran-containing solvent, cooling to a temperature below 15° C., isolating and drying the crystals.

34. A method of preparing the crystalline 1,2-propandiol solvate of tiotropium bromide of claim 16, comprising drying crystalline tiotropium bromide monohydrate at a temperature of 60-90° C., dissolving the crystalline tiotropium bromide monohydrate in a 1,2-propandiol-containing solvent to form a solution, holding the solution at a temperature in the range of 30-70° C., cooling the solution to a temperature below 15° C., isolating and drying the crystals.

35. A method of preparing the crystalline anisol solvate of tiotropium bromide of claim 1, comprising drying crystalline tiotropium bromide monohydrate at a temperature of 60-90° C., dissolving the crystalline tiotropium bromide monohydrate in an anisol-containing solvent to form a solution, holding the solution at a temperature in the range of 30-70° C., cooling the solution to a temperature below 15° C., isolating and drying the crystals.

36. A method of preparing the crystalline tetrahydropyran solvate of tiotropium bromide of claim 28, comprising drying crystalline tiotropium bromide monohydrate at a temperature of 60-90° C., dissolving the crystalline tiotropium bromide monohydrate in a tetrahydropyran-containing solvent to form a solution, holding the solution at a temperature in the range of 30-70° C., cooling the solution to a temperature below 15° C., isolating and drying the crystals.

37. A method of preparing the crystalline N,N-dimethylformamide solvate of tiotropium bromide of claim 10, comprising drying crystalline tiotropium bromide monohydrate at a temperature of 60-90° C., suspending the crystalline tiotropium bromide monohydrate in a N,N-dimethylformamide-containing solvent to form a solution, adding an anti-solvent to the solution, isolating and drying the crystals.

38. A method of preparing the crystalline N,N-dimethylacetamide solvate of tiotropium bromide of claim 7, comprising drying crystalline tiotropium bromide monohydrate at a temperature of 60-90° C., suspending the crystalline tiotropium bromide monohydrate in a N,N-dimethylacetamide-containing solvent to form a solution, adding anti-solvent to the solution, isolating and drying the crystals.

39. A method of preparing the crystalline tetrahydrofuran solvate of tiotropium bromide of claim 25, comprising dissolving crystalline tiotropium bromide monohydrate in an acetone-containing solvent, slowly evaporating the solvent to form a solid, treating the solid with a tetrahydrofuran-containing solvent to form a solution, holding the solution at a temperature in the range of 30-70° C., cooling the solution to a temperature below 15° C., isolating and drying the crystals.

40. A method of preparing the crystalline tert.-butanol solvate of tiotropium bromide of claim 22, comprising dissolving crystalline tiotropium bromide monohydrate in an acetone-containing solvent, slowly evaporating the solvent to form a solid, treating the solid with a tert-butanol-containing solvent to form a solution, holding the solution at a temperature in the range of 30-70° C., cooling the solution to a temperature below 15° C., isolating and drying the crystals.

41. A method of preparing the crystalline pyridine solvate of tiotropium bromide of claim 19, comprising dissolving crystalline tiotropium bromide monohydrate in an acetone-containing solvent, slowly evaporating the solvent to form a solid, treating the solid with a pyridine-containing solvent to form a solution, holding the solution at a temperature in the range of 30-70° C., cooling the solution to a temperature below 15° C., isolating and drying the crystals.

42. A crystalline tiotropium bromide anhydrate characterized by an X-ray powder diffraction pattern with a characteristic value d=21.91 Å.

43. The crystalline tiotropium bromide anhydrate according to claim 42, further characterized by an X-ray powder diffraction pattern with characteristic values d=15.08 Å and 21.91 Å.

44. The crystalline tiotropium bromide anhydrate according to claim 43, further characterized by an X-ray powder diffraction with characteristic values d=18.07 Å, 15.08 Å and 21.91 Å.

45. A method of preparing the crystalline tiotropium bromide anhydrate of claim 42, comprising dissolving crystalline tiotropium bromide monohydrate in a suitable solvent, heating to a temperature in the range of about 30-70° C., cooling to a temperature below 15° C. to form the crystalline tiotropium bromide anhydrate, isolating and drying the crystals.

46. The method according to claim 45, wherein the suitable solvent is a solvent mixture comprising N,N-dimethylacetamide.

47. A crystalline 1,4-dioxane solvate of tiotropium bromide characterized by an X-ray powder diffraction pattern with a characteristic value d=21.33 Å.

48. The crystalline 1,4-dioxane solvate of tiotropium bromide according to claim 47, further characterized by an X-ray powder diffraction pattern with characteristic values d=18.09 Å and 21.33 Å.

49. The crystalline 1,4-dioxane solvate of tiotropium bromide according to claim 48, further characterized by an X-ray powder diffraction with characteristic values d=15.27 Å, 18.09 Å and 21.33 Å.

50. A method of preparing the crystalline dioxane solvate of tiotropium bromide of claim 47, comprising drying crystalline tiotropium bromide monohydrate at a temperature of 60-90° C., dissolving the crystalline tiotropium bromide monohydrate in a methanol-containing solvent to form a solution, adding the solution to a dioxane-containing solvent, cooling to a temperature below 15° C., isolating and drying the crystals.

51. A crystalline ethanol solvate of tiotropium bromide characterized by an X-ray powder diffraction pattern with a characteristic value d=21.39 Å.

52. The crystalline ethanol solvate of tiotropium bromide according to claim 51, further characterized by an X-ray powder diffraction pattern with characteristic values d=18.12 Å and 21.39 Å.

53. The crystalline ethanol solvate of tiotropium bromide according to claim 52, further characterized by an X-ray powder diffraction with characteristic values d=19.91 Å, 18.12 Å and 21.39 Å.

54. A method of preparing the crystalline ethanol solvate of tiotropium bromide of claim 51, comprising drying crystalline tiotropium bromide monohydrate at a temperature of 60-90° C., dissolving the crystalline tiotropium bromide monohydrate in an ethanol-containing solvent, cooling to a temperature below 0° C., isolating and drying the crystals.

55. A crystalline methanol solvate of tiotropium bromide characterized by an X-ray powder diffraction pattern with a characteristic value d=19.70 Å.

56. The crystalline methanol solvate of tiotropium bromide according to claim 55, further characterized by an X-ray powder diffraction pattern with characteristic values d=21.44 Å and 19.70 Å.

57. The crystalline methanol solvate of tiotropium bromide according to claim 56, further characterized by an X-ray powder diffraction with characteristic values d=13.43 Å, 21.44 Å and 19.70 Å.

58. A method of preparing the crystalline methanol solvate of tiotropium bromide of claim 55, comprising drying crystalline tiotropium bromide monohydrate at a temperature of 60-90° C., dissolving the crystalline tiotropium bromide monohydrate in a methanol-containing solvent, cooling to a temperature below 0° C., isolating and drying the crystals.

* * * * *